(12) United States Patent
Brendel et al.

(10) Patent No.: US 6,221,866 B1
(45) Date of Patent: Apr. 24, 2001

(54) INDANYL-SUBSTITUTED BENZENECARBOXAMIDES, PROCESSES FOR THEIR PREPARATION, THEIR USE AS A MEDICAMENT, AND PHARMACEUTICAL FORMULATIONS CONTAINING THEM

(75) Inventors: Joachim Brendel, Bad Vilbel; Uwe Gerlach, Hattersheim; Hans Ulrich Stilz, Frankfurt; Hans-Jochen Lang, Hofheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/603,436

(22) Filed: Jun. 23, 2000

(30) Foreign Application Priority Data

Jun. 25, 1999 (DE) ................................................ 199 29 076

(51) Int. Cl.[7] ........................ A61K 31/535; A61K 31/47; A61K 31/445; A61K 31/18
(52) U.S. Cl. ........................ 514/237.8; 514/310; 514/319; 514/603; 544/159; 546/153; 546/205; 564/85; 564/86; 564/87
(58) Field of Search ................................ 514/237.8, 310, 514/319, 603; 544/159; 546/153, 205; 564/85, 86, 87

(56) References Cited

U.S. PATENT DOCUMENTS

| | | |
|---|---|---|
| 5,043,347 | 8/1991 | Clemence et al. .................. 514/409 |
| 5,234,944 | 8/1993 | Clemence et al. .................. 514/429 |
| 5,348,971 | 9/1994 | Clemence et al. .................. 514/428 |
| 5,877,221 | 3/1999 | Cohen et al. ....................... 514/629 |
| 6,015,822 | 1/2000 | Brendel et al. ..................... 514/357 |

FOREIGN PATENT DOCUMENTS

| | | |
|---|---|---|
| 0 258 096 A2 | 3/1988 | (EP) . |
| 0 374 054 A1 | 6/1990 | (EP) . |
| 0 915 087 A2 | 5/1999 | (EP) . |
| 95/18617 | 7/1995 | (WO) . |

Primary Examiner—Peter O'Sullivan
(74) Attorney, Agent, or Firm—Finnegan, Henderson, Farabow, Garrett and Dunner, L.L.P.

(57) ABSTRACT

Compounds of formula I

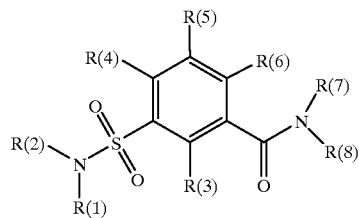

in which R(1) to R(8) have the meanings stated in the claims, act on the Kv1.5 potassium channel, and inhibit a potassium current, referred to as "ultra-rapidly activating delayed rectifier," in the human atrium. They are therefore very particularly suitable as novel antiarrhythmic active substances, in particular for the treatment and prophylaxis of atrial arrhythmias, e.g., atrial fibrillation or atrial flutter.

16 Claims, No Drawings

INDANYL-SUBSTITUTED BENZENECARBOXAMIDES, PROCESSES FOR THEIR PREPARATION, THEIR USE AS A MEDICAMENT, AND PHARMACEUTICAL FORMULATIONS CONTAINING THEM

The invention relates to compounds of formula I

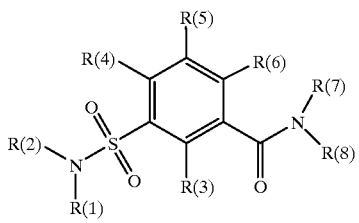

in which R(8) is either a 1-indanyl radical of formula II or a 2-indanyl radical of formula III

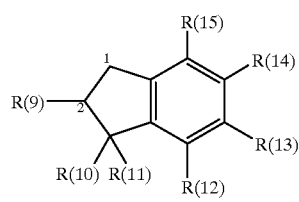

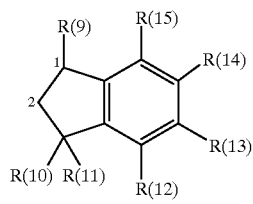

and in which R(1), R(2), R(3), R(4), R(5), R(6), R(7), R(9), R(10), R(11), R(12), R(13), R(14), and R(15) have the meanings stated below, their preparation, and their use, in particular in medicaments.

Compounds according to the invention act on the so-called Kv1.5 potassium channel and inhibit a potassium current, referred to as "ultra-rapidly activating delayed rectifier," in the human atrium. The compounds are therefore very particularly suitable as novel antiarrhythmic active substances, in particular for the treatment and prophylaxis of atrial arrhythmias, e.g., atrial fibrillation or atrial flutter.

Atrial fibrillation (AF) and atrial flutter are the most frequent persistent cardiac arrhythmias. They occur increasingly with increasing age and frequently lead to fatal consequences, such as, for example, a cerebrovascular accident. AF affects about 1 million Americans annually and leads to more than 80,000 strokes every year in the USA. The class I and III antiarrhythmic drugs commonly used at present reduce the rate of recurrence of AF but, owing to their potential proarrhythmic side effects, are used only to a limited extent. There is therefore a considerable medical necessity for the development of better medicaments for the treatment of atrial arrhythmias (S. Nattel, "Newer developments in the management of atrial fibrillation," Am. Heart J. 130 (1995;) 1094–1106).

It was found that most supraventricular arrhythmias are based on so-called "re-entry" excitation thresholds. Such re-entries occur when the heart tissue has slow conductivity and at the same time very short refractory periods. Increasing the myocardial refractory time by lengthening the action potential is a recognized mechanism for terminating arrhythmias and for preventing their occurrence (T. J. Colatsky et al., "Potassium channels as targets for antiarrhythmic drug action," Drug Dev. Res. 19 (1990) 129–140). The length of the action potential is essentially determined by the extent of repolarizing K+ currents that flow out of the cell via various.; K+channels. Particularly great importance here is attributed to the so-called "delayed rectifier" $I_K$, which consists of three different components: $IK_r$, $IK_s$, and $IK_{ur}$.

Most known class III antiarrhythmic drugs (e.g., Dofetilide, E4031, and d-Sotalol) predominantly or exclusively block the fast-activating potassium channel $IK_r$, which is detectable both in the cells of the human ventricle and in the atrium. However, it has been found that these compounds give rise to a high proarrhythmic risk at low or normal heart rates, in particular arrhythmias referred to as "Torsades de pointes" having been observed (D. M. Roden, "Current status of class III antiarrhythmic drug therapy," Am. J. Cardiol. 72 (1993) 44B–49B). In addition to this high, sometimes fatal risk at low rate, the $IK_r$ blockers were found to decline in activity under the conditions of tachycardia, precisely where the activity is required ("negative use-dependence").

While some of these disadvantages can possibly be overcome by blockers of the slowly activating component ($IK_s$), their activity has not been demonstrated to date, since no clinical studies with $IK_s$ channel blockers are known.

The "particularly rapidly" activating and very slowly inactivating component of tile delayed rectifier $IK_{ur}$ (=ultra-rapidly activating delayed rectifier), which corresponds to the Kv1.5 channel, plays a particularly major role for the repolarization time in the human atrium. Compared with the inhibition of $IK_r$ or $IK_s$, inhibition of the $Ik_{ur}$ potassium outward current is thus a particularly effective method for lengthening the atrial action potential and hence for terminating or preventing atrial arrhythmias.

In contrast to $IK_r$ and $IK_s$, which also occur in the human ventricle, the $IK_{ur}$ plays an important role in the human atrium but not in the ventricle. For this reason, on inhibition of the $IK_{ur}$ current, in contrast to the blockage of $IK_r$ or $IK_s$, the risk of a proarrythmic effect on the ventricle is ruled out from the outset. (Z. Wang et al., "Sustained Depolarisation-Induced Outward Current in Human Atrial Myocytes," Circ. Res. 73 (1993) 1061–1076; G. -R. Li et al., "Evidence for Two Components of Delayed Rectifier K+-Current in Human Ventricular Myocytes," Circ. Res. 78 (1996) 689–696; G. J. Amos et al., "Differences between outward currents of human atrial and subepicardial ventricular myocytes," J. Physiol. 491 (1996) 31–50).

Selective blockers of the $IK_{ur}$ or Kv1.5 channel have not been described to date in the literature. Although a blocking effect on the Kv1.5 channel has been described for numerous pharmaceutical active substances (e.g., Tedisamil, Bupivacaine, or Sertindole), the Kv1.5 blockage in each case constitutes only a side effect here, alongside other principal effects of the substances. WO 98 04 521 claims, as potassium channel blockers, aminoindanes which block the Kv1.5 channel. However, an equipotent action on the Kv1.3 channel is also described for these compounds. Blockage of the Kv1.3 channel, which plays a role in human T-lymphocytes, has an immunosuppressive effect, which is undesirable as a side effect of an antiarrhythmic drug to be administered for a chronic condition. Applications WO 98 18 475 and WO 98 18 476 claim the use of various pyridazinones and phosphine oxides as antiarrhythmic drugs, which are said to act by blocking the $IK_{ur}$. However, these compounds were originally (WO 96 25 936) also described as immunosuppressive drugs, so that their medical usability for the treatment of atrial arrhythmias appears doubtful.

It has now been found that compounds according to the invention are potent blockers of the human Kv1.5 channel. They can therefore be used as novel antiarrhythmic drugs having a particularly advantageous safety profile. In particular, the compounds are suitable for the treatment of supraventricular arrhythmias, e.g., AF or atrial flutter.

Compounds according to the invention, of formula I, were not previously known. Some structurally related indane derivatives are described in the applications EP 258 096 and EP 374 054. However, the compounds claimed there differ from the compounds according to the invention in this application in that, in said applications, R(9) is a basic amino substituent. Moreover, only unsubstituted sulfonamides (R(1) and R(2)=H) are described there, whereas it has been found here that it is precisely substituted sulfonamides that are particularly effective blockers of the Kv1.5 channel.

The present invention relates to compounds of formula I

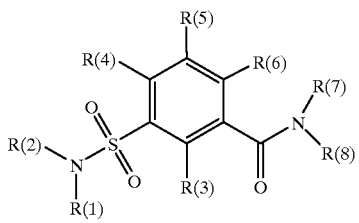

I in which R(8) is either a 1-indanyl radical of formula II or a 2-indanyl radical of formula III

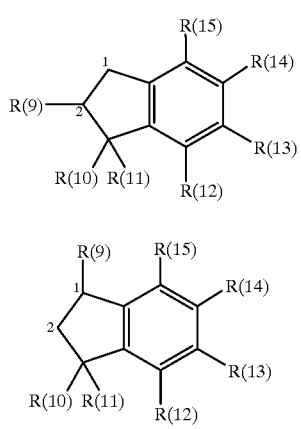

II

III and in which:

R(1) and R(2), independently of one another, are R(20)-$C_rH_{2r}$,
  where at least one $CH_2$ group of the group $C_rH_{2r}$ is optionally replaced by —O—, —CH=CH—, —C≡C—, —CO—, —CO—O—, —O—CO—, —S—, —SO—, —SO$_2$—, —NR(21)—, or —CONR(21);
  R(21) is hydrogen or alkyl having 1, 2, or 3 carbon atoms;
  R(20) is H, $CH_3$, $CH_2F$, $CHF_2$, $CF_3$, $C_2F_5$, $C_3F_7$, cycloalkyl having 3, 4, 5, 6, 7, or 8 carbon atoms, NR(22)R(23), —CONR(22)R(23), —OR(24), —COOR(24), phenyl, or an N-containing heterocycle having 1, 2, 3, 4, 5, 6, 7, 8, or 9 carbon atoms,
    where phenyl and the N-containing heterocycle are unsubstituted or substituted by 1 or 2 substituents selected from F, Cl, Br, I, $CF_3$, $NO_2$, CN, $NH_2$, OH, methyl, ethyl, hydroxymethyl, hydroxyethyl, methoxy, dimethylamino, sulfamoyl, methylsulfonyl, and methylsulfonylamino;
  R(22) and R(23), independently of one another, are hydrogen or alkyl having 1, 2, 3, or 4 carbon atoms; or
  R(22) and R(23) together form a chain of 4 or 5 methylene groups, of which one $CH_2$ group is optionally replaced by —O—, —S—, —NH—, —N(methyl)—, or —N(benzyl)—;
  R(24) is hydrogen or alkyl having 1, 2, or 3 carbon atoms;
  r is 0, 1, 2, 3, 4, 5, 6, 7, or 8;
or
R(1) and R(2) together form a chain of 4 or 5 methylene groups, of which one $CH_2$ group is optionally replaced by —O—, —S—, —NH—, —N(methyl)—, or —N(benzyl)—;
R(3), R(4), R(5), and R(6), independently of one another, are hydrogen, F, Cl, Br, I, alkyl having 1, 2, 3, 4, or 5 carbon atoms, cycloalkyl having 3, 4, 5, 6, 7, or 8 carbon atoms, CN, $CF_3$, $NO_2$, OR(25), or NR(26)R(27);
R(25) is hydrogen, alkyl having 1, 2, 3, or 4 carbon atoms, a fluorinated alkyl radical of formula —$C_xH_{2x}CF_yH_{3-y}$, or phenyl,
  in which phenyl is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methyl-sulfonyl, and methylsulfonylamino;
x is 0, 1, 2, or 3;
y is 1, 2, or 3;
R(26) and R(27), independently of one another, are hydrogen or alkyl having 1, 2, 3, or 4 carbon atoms; or
R(26) and R(27) together form a chain of 4 or 5 methylene groups, of which one $CH_2$ group is optionally replaced by —O—, —S—, —NH—, —N(methyl)—, or —N(benzyl)—;
R(7) is hydrogen or alkyl having 1, 2, 3, or 4 carbon atoms;
R(9) is hydrogen, OR(28), or OCOR(28);
R(28) is hydrogen or alkyl having 1, 2, 3, or 4 carbon atoms;
R(10) and R(11), independently of one another, are hydrogen or alkyl having 1, 2, 3, or 4 carbon atoms;
R(12), R(13), R(14), and R(15), independently of one another, are hydrogen, F, Cl, Br, I, alkyl having 1, 2, 3, 4, or 5 carbon atoms, cycloalkyl having 3, 4, 5, 6, 7, or 8 carbon atoms, —CN, —$CF_3$, —$C_2F_5$, —$C_3F_7$, —$N_3$, —$NO_2$, —Y—$C_sH_{2s}$—R(29), phenyl, thienyl, furyl, or an N-containing heterocycle having 1, 2, 3, 4, 5, 6, 7, 8, or 9 carbon atoms,
  where phenyl, thienyl, furyl, and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;
Y is —O—, —CO—, —CO—O—, —O—CO—, —S—, —SO—, —SO$_2$—, —O—SO$_2$—, —SO$_2$NR(30)—, —CONR(30)—, or —NR(30)CO—, where the link to the backbone is in each case via the atom on the left; R(30) is hydrogen or alkyl having 1, 2, or 3 carbon atoms;

s is 0, 1, 2, 3, 4, 5, or 6;

R(29) is hydrogen, methyl, $CF_3$, $C_2F_5$, $C_3F_7$, cycloalkyl having 3, 4, 5, 6, 7, or 8 carbon atoms, —OR(31), —COOR(31), —NR(32)R(33), —CONR(32)R(33), phenyl, or an N-containing heterocycle having 1, 2, 3, 4, 5, 6, 7, 8, or 9 carbon atoms,
  where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;

R(31) is hydrogen or alkyl having 1, 2, or 3 carbon atoms;

R(32) and R(33), independently of one another, are hydrogen or alkyl having 1, 2, 3, or 4 carbon atoms;

or

R(32) and R(33) together form a chain of 4 or 5 methylene groups, of which one $CH_2$ group is optionally replaced by —O—, —S—, —NH—, —N($CH_3$)—, or —N(benzyl)—;

or a physiologically tolerated salt thereof.

Compounds of formula I having the abovementioned meanings, but where at least one of the radicals R(1) and R(2) is other than hydrogen are preferred.

Particularly preferred are compounds of formula I in which R(8) is either a 1-indanyl radical of formula II or a 2-indanyl radical of formula III and in which:

R(1) is hydrogen;

R(2) is R(20)—$C_rH_{2r}$,
  where at least one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(21)—, or —CONR(21);

R(21) is hydrogen or alkyl having 1, 2, or 3 carbon atoms;

R(20) is $CH_3$, $CH_2F$, $CHF_2$, $CF_3$, $C_2F_5$, $C_3F_7$, cycloalkyl having 3, 4, 5, 6, 7, or 8 carbon atoms, NR(22)R(23), —CONR(22)R(23), —OR(24), —COOR(24), phenyl, or an N-containing heterocycle having 1, 2, 3, 4, 5, 6, 7, 8, or 9 carbon atoms,
  where phenyl and the N-containing heterocycle are unsubstituted or substituted by 1 or 2 substituents selected from F, Cl, Br, I, $CF_3$, $NO_2$, CN, $NH_2$, OH, methyl, ethyl, hydroxymethyl, hydroxyethyl, methoxy, dimethylamino, suffamoyl, methylsuffonyl, and methylsulfonylamino;

R(22) and R(23), independently of one another, are hydrogen or alkyl having 1, 2, 3, or 4 carbon atoms;

or

R(22) and R(23) together form a chain of 4 or 5 methylene groups, of which ore $CH_2$ group is optionally replaced by —O—, —S—, —NH—, —N(methyl)—, or —N(benzyl)—;

R(24) is hydrogen or alkyl having 1, 2, or 3 carbon atoms;

r is 0, 1, 2, 3, 4, 5, 6, 7, or 8;

R(3), R(4), R(5), and R(6), independently of one another, are hydrogen, F, Cl, Br, I, alkyl having 1, 2, 3, 4, or 5 carbon atoms, cycloalkyl having 3, 4, 5, 6, 7, or 8 carbon atoms, CN, $CF_3$, $NO_2$, OR(25), or NR(26)R(27);

R(25) is hydrogen, alkyl having 1, 2, 3, or 4 carbon atoms, a fluorinated alkyl radical of formula —$C_xH_{2x}CF_yH_{3-y}$, or phenyl,
  in which phenyl is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methyl-sulfonyl, and methylsulfonylamino;

x is 0, 1, 2, or 3;

y is 1, 2, or 3;

R(26) and R(27), independently of one another, are hydrogen or alkyl having 1, 2, 3, or 4 carbon atoms;

or

R(26) and R(27) together form a chain of 4 or 5 methylene groups, of which one $CH_2$ group is optionally replaced by —O—, —S—, —NH—, —N(methyl)—, or —N(benzyl)—;

R(7) is hydrogen or alkyl having 1, 2, 3, or 4 carbon atoms;

R(9) is hydrogen, OR(28), or OCOR(28);

R(28) is hydrogen or alkyl having 1, 2, 3, or 4 carbon atoms;

R(10) and R(11), independently of one another, are hydrogen or alkyl having 1, 2, 3, or 4 carbon atoms;

R(12), R(13), R(14), and R(15), independently of one another, are hydrogen, F, Cl, Br, I, alkyl having 1, 2, 3, 4, or 5 carbon atoms, cycloalkyl having 3, 4, 5, 6, 7, or 8 carbon atoms, —CN, —$CF_3$, —$C_2F_5$, —$C_3F_7$, —$N_3$, —$NO_2$, —Y—$C_sH_{2s}$—R(29), phenyl, thienyl, furyl, or an N-containing heterocycle having 1, 2, 3, 4, 5, 6, 7, 8, or 9 carbon atoms,
  where phenyl, thienyl, furyl, and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsuffonyl, and methylsulfonylamino;

Y is —O—, —CO—, —CO—O—, —O—CO—, —S—, —SO—, —$SO_2$—, —O—$SO_2$—, —$SO_2$NR(30)—, —CONR(30)—, or —NR(30)CO—, where the link to the backbone is in each case via the atom on the left; R(30) is hydrogen or alkyl having 1, 2, or 3 carbon atoms;

s is 0, 1, 2, 3, 4, 5, or 6;

R(29) is hydrogen, methyl, $CF_3$, $C_2F_5$, $C_3F_7$, cycloalkyl having 3, 4, 5, 6, 7, or 8 carbon atoms, —OR(31), —COOR(31), —NR(32)R(33), —CONR(32)R(33), phenyl, or an N-containing heterocycle having 1, 2, 3, 4, 5, 6, 7, 8, or 9 carbon atoms,
  where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;

R(31) is hydrogen or alkyl having 1, 2, or 3 carbon atoms;

R(32) and R(33), independently of one another, are hydrogen or alkyl having 1, 2, 3, or 4 carbon atoms;

or

R(32) and R(33) together form a chain of 4 or 5 methylene groups, of which one $CH_2$ group is optionally replaced by —O—, —S—, —NH—, —N($CH_3$)—, or —N(benzyl)—;

or a physiologically tolerated salt thereof.

Very particularly preferred are compounds of formula I in which R(8) is a 1-indanyl radical of formula II, i.e., compounds of formula Ia

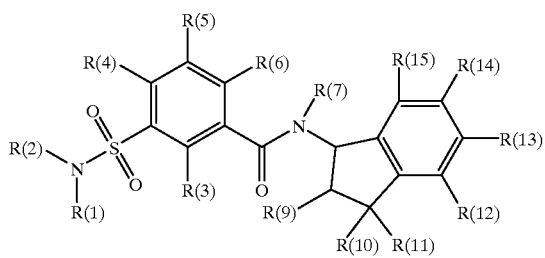

in which:
R(1) is hydrogen;
R(2) is R(20)—CY$_r$H$_{2r}$,
  where at least one CH$_2$ group of the group C$_r$H$_{2r}$ is optionally replace[]d by —O—, —CH=CH—, —C≡C—, —CO—, —CO—O—, —O—CO—, —S—, —SO—, —SO$_2$—, —NR(21)—, or —CONR(21);
  R(21) is hydrogen or alkyl having 1, 2, or 3 carbon atoms;
  R(20) is CH$_3$, CH$_2$F, CHF$_2$, CF$_3$, C$_2$F$_5$, C$_3$F$_7$, cycloalkyl having 3, 4, 5, 6, 7, or 8 carbon atoms, NR(22)R(23), —CONR(22)R(23), —OR(24), —COOR(24), phenyl, or an N-containing heterocycle having 1, 2, 3, 4, 5, 6, 7, 8, or 9 carbon atoms,
    where phenyl and the N-containing heterocycle are unsubstituted or substituted by 1 or 2 substituents selected from F, Cl, Br, I, CF$_3$, NO$_2$, CN, NH$_2$, OH, methyl, ethyl, hydroxymethyl, hydroxyethyl, methoxy, dimethylamino, sulfamoyl, methylsulfonyl, and methylsulfonylamino;
    R(22) and R(23), independently of one another, are hydrogen or alkyl having 1, 2, 3, or 4 carbon atoms; or
    R(22) and R(23) together form a chain of 4 or 5 methylene groups, of which one CH$_2$ group is optionally replaced by —O—, —S—, —NH—, —N(methyl)—, or —N(benzyl)—;
  R(24) is hydrogen or alkyl having 1, 2, or 3 carbon atoms;
  r is 0, 1, 2, 3, 4, or 5;
R(3), R(4), R(5), and R(6), independently of one another, are hydrogen, F, Cl, Br, I, alkyl having 1, 2, 3, 4, or 5 carbon atoms, cycloalkyl having 3, 4, 5, 6, 7, or 8 carbon atoms, CN, CF$_3$, NO$_2$, or OR(25);
  R(25) is hydrogen, alkyl having 1, 2, 3, or 4 carbon atoms, a fluorinated alkyl radical of formula —C$_x$H$_{2x}$CF$_y$H$_{3-y}$, or phenyl,
    in which phenyl is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methyl-sulfonyl, and methylsulfonylamino;
    x is 0, 1, 2, or 3;
    y is 1, 2, or 3;
R(7) is hydrogen or alkyl having 1, 2, 3, or 4 carbon atoms;
R(9) is hydrogen, OR(28), or OCOR(28);
  R(28) is hydrogen or alkyl having 1, 2, 3, or 4 carbon atoms;
R(10) and R(11), independently of one another, are hydrogen or alkyl having 1, 2, 3, or 4 carbon atoms;

R(12), R(13), R(14), and R(15), independently of one another, are hydrogen, F, Cl, Br, I, alkyl having 1, 2, 3, 4, or 5 carbon atoms, cycloalkyl having 3, 4, 5, 6, 7, or 8 carbon atoms, —CN, —CF$_3$, —C$_2$F$_5$, —C$_3$F$_7$, —NO$_2$, —Y—C$_s$H$_{2s}$—R(29), phenyl, thienyl, furyl, or an N-containing heterocycle having 1, 2, 3, 4, 5, 6, 7, 8, or 9 carbon atoms,
  where phenyl, thienyl, furyl, and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino;
Y is —O—, —CO—, —CO—O—, —O—CO—, —S—, —SO—, —SO$_2$—, —O—SO$_2$—, —SO$_2$NR(30)—, —CONR(30)—, or —NR(30)CO—, where the link to the backbone is in each case via the atom on the left;
R(30) is hydrogen or alkyl having 1, 2, or 3 carbon atoms;
s is 0, 1, 2, 3, 4, 5, or 6;
R(29) is hydrogen, methyl, CF$_3$, C$_2$F$_5$, C$_3$F$_7$, cycloalkyl having 3, 4, 5, 6, 7, or 8 carbon atoms, —OR(31), —COOR(31), —NR(32)R(33), —CONR(32)R(33), phenyl, or an N-containing heterocycle having 1, 2, 3, 4, 5, 6, 7, 8, or 9 carbon atoms,
  where phenyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino;
  R(31) is hydrogen or alkyl having 1, 2, or 3 carbon atoms;
  R(32) and R(33), independently of one another, are hydrogen or alkyl having 1, 2, 3, or 4 carbon atoms; or
  R(32) and R(33) together form a chain of 4 or 5 methylene groups, of which one CH$_2$ group is optionally replaced by —O—, —S—, —NH—, —N(CH$_3$)—, or —N(benzyl)—;
or a physiologically tolerated salt thereof.
Especially preferred are compounds of formula Ia in which:
R(1) is hydrogen;
R(2) is R(20)—C$_r$H$_{2r}$;
  R(20) is CH$_3$, CH$_2$F, CHF$_2$, CF$_3$, cycloalkyl having 3, 4, 5, 6, 7, or 8 carbon atoms, —CONR(22)R(23), —OR(24), —COOR(24), or phenyl,
    where phenyl is unsubstituted or substituted by 1 or 2 substituents selected from F, Cl, Br, CF$_3$, NO$_2$, CN, OH, methyl, ethyl, hydroxymethyl, hydroxyethyl, methoxy, dimethylamino, sulfamoyl, methylsulfonyl, and methylsulfonylamino;
    R(22) and R(23), independently of one another, are hydrogen or alkyl having 1, 2, 3, or 4 carbon atoms; or
    R(22) and R(23) together form a chain of 4 or 5 methylene groups, of which one CH$_2$ group is optionally replaced by —O—, —S—, —NH—, —N(methyl)—, or —N(benzyl)—;
    R(24) is hydrogen or alkyl having 1, 2, or 3 carbon atoms;
  r is 0, 1, 2, 3, 4, or 5;
R(3), R(4), R(5), and R(6), independently of one another, are hydrogen, F, Cl, Br, I, alkyl having 1, 2, 3, 4, or 5 carbon atoms, cycloalkyl having 3, 4, 5, 6, 7, or 8 carbon atoms, CN, CF$_3$, NO$_2$, or OR(25);

R(25) is hydrogen, alkyl having 1, 2, 3, or 4 carbon atoms, a fluorinated alkyl radical of formula —$C_xH_{2x}CF_yH_{3-y}$, or phenyl,
in which phenyl is unsubstituted or substituted by 1 or 2 substituents selected from F, Cl, Br, $CF_3$, $NO_2$, CN, OH, methyl, ethyl, methoxy, dimethylamino, sulfamoyl, methylsulfonyl, and methylsulfonylamino;
x is 0, 1, 2, or 3;
y is 1, 2, or 3;
R(7) is hydrogen or alkyl having 1, 2, 3, or 4 carbon atoms;
R(9) is hydrogen or OR(28);
R(28) is hydrogen or alkyl having 1, 2, 3, or 4 carbon atoms;
R(10) and R(11), independently of one another, are hydrogen or alkyl having 1, 2, 3, or 4 carbon atoms;
R(12), R(13), R(14), and R(15), independently of one another, are hydrogen, F, Cl, Br, I, alkyl having 1, 2, 3, 4, or 5 carbon atoms, cycloalkyl having 3, 4, 5, 6, 7, or 8 carbon atoms, CN, $CF_3$, —$NO_2$, or —Y—$C_sH_{2s}$—R(29);
Y is —O—, —CO—, —CO—O—, —O—CO—, —S—, —SO—, —$SO_2$—, —O—$SO_2$—, —$SO_2$NR(30)—, —CONR(30)—, or —NR(30)CO—, where the link to the backbone is in each case via the atom on the left;
R(30) is hydrogen or alkyl having 1, 2, or 3 carbon atoms;
s is 0, 1, 2, 3, 4, or 5;
R(29) is hydrogen, methyl, $CF_3$, —OR(31), —COOR(31), —NR(32)R(33), —CONR(32)R(33), or phenyl, where phenyl is unsubstituted or substituted by 1 or 2 substituents selected from F, Cl, Br, $CF_3$, $NO_2$, CN, OH, methyl, ethyl, methoxy, dimethylamino, sulfamoyl, methylsulfonyl, and methylsulfonylamino;
R(31) is hydrogen or alkyl having 1, 2, or 3 carbon atoms;
R(32) and R(33), independently of one another, are hydrogen or alkyl having 1, 2, 3, or 4 carbon atoms; or
R(32) and R(33) together form a chain of 4 or 5 methylene groups, of which one $CH_2$ group is optionally replaced by —O—, —S—, —NH—, —N($CH_3$)—, or —N(benzyl)—;
or a physiologically tolerated salt thereof.

Alkyl radicals and alkylene radicals may be straight-chained or branched. This also applies to the alkylene radicals of formulae $C_rH_{2r}$, $C_sH_{2s}$, and $C_xH_{2x}$. Alkyl radicals and alkylene radicals may also be straight-chained or branched if they are substituted or are contained in other radicals, e.g., in an alkoxy radical or in an alkylmercapto radical or in a fluorinated alkyl radical. Examples of alkyl radicals are methyl, ethyl, n-propyl, isopropyl, n-butyl, isobutyl, sec-butyl, tert-butyl, n-pentyl, isopentyl, neopentyl, n-hexyl, 3,3-dimethylbutyl, heptyl, octyl, nonyl, decyl, undecyl, dodecyl, tridecyl, tetradecyl, pentadecyl, hexadecyl, heptadecyl, octadecyl, nonadecyl, and eicosyl. The divalent radicals derived from these radicals, e.g., methylene, 1,1-ethylene, 1,2-ethylene, 1,1-propylene, 1,2-propylene, 2,2-propylene, 1,3-propylene, 1,4-butylene, 1,5-pentylene, 2,2-dimethyl-1,3-propylene, and 1,6-hexylene, are examples of alkylene radicals.

Cycloalkyl radicals can likewise be branched. Examples of cycloalkyl radicals having 3 to 8 carbon atoms are cyclopropyl, cyclobutyl, 1-methylcyclopropyl, 2-methylcyclopropyl, cyclopentyl, 2-methylcyclobutyl, 3-methylcyclobutyl, cyclopentyl, cyclohexyl, 2-methylcyclohexyl, 3-methylcyclohexyl, 4-methylcyclohexyl, cycloheptyl, and cyclooctyl.

N-containing heterocycles having 1, 2, 3, 4, 5, 6, 7, 8, or 9 carbon atoms are in particular the aromatic systems 1-, 2-, or 3-pyrrolyl, 1-, 2-, 4-, or 5-imidazolyl, 1-, 3-, 4-, or 5-pyrazolyl, 1,2,3triazol-1-, -4-, or -5-yl, 1,2,4-triazol-1-, -3-, or -5-yl, 1- or 5-tetrazolyl, 2-, 4-, or 5-oxazolyl, 3-, 4-, or 5-isoxazolyl, 1,2,3-oxadiazol-4- or -5-yl, 1,2,4-oxadiazol-3-or -5-yl, 1,3,4-oxadiazol-2-yl or -5-yl, 2-, 4-, or 5-thiazolyl, 3-, 4-, or 5-isothiazolyl, 1,3,4-thiadiazol-2- or -5-yl, 1,2,4-thiadiazol-3- or -5-yl, 1,2,3-thiadiazol4- or -5-yl, 2-, 3-, or 4-pyridyl, 2-, 4-, 5-, or 6-pyrimidinyl, 3- or 4-pyridazinyl, pyrazinyl, 1-, 2-, 3-, 4-, 5-, 6-, or 7-indolyl, 1-, 2-, 4-, or 5-benzimidazolyl, 1-, 3-, 4-, 5-, 6-, or 7-indazolyl, 2-, 3-, 4-, 5-, 6-, 7-, or 8-quinolyl, 1-, 3-, 4-, 5-, 6-, 7-, or 8-isoquinolyl, 2-, 4-, 5-, 6-, 7-, or 8-quinazolinyl, 3-, 4-, 5-, 6-, 7-, or 8-cinnolinyl, 2-, 3-, 5-, 6-, 7-, or 8-quinoxalinyl, or 1-, 4-, 5-, 6-, 7-, or 8-phthalazinyl.

The N-containing heterocycles pyrrolyl, imidazolyl, quinolyl, pyrazolyl, pyridyl, pyrazinyl, pyrimidinyl, and pyridazinyl are particularly preferred.

Thienyl is both 2- and 3-thienyl.

Monosubstituted phenyl radicals may be substituted in the 2-, 3-, or 4-position, or disubstituted in the 2,3-, 2,4-, 2,5-, 2,6-, 3,4-, or 3,5-position. The same applies in context to the N-containing heterocycles or the thiophene radical.

In the case of disubstitution of a radical, the substituents may be identical or different.

The term "where the link to the backbone is in each case via the atom on the left" for the description of Y means that Y is bound to the phenyl ring via its left bond and its right bond is affixed to the —$C_sH_{2s}$—R(29) substituent.

If compounds of formula I contain one or more acidic or basic groups or one or more basic heterocycles, the corresponding physiologically or toxicologically tolerated salts are also the subject of the invention, in particular the pharmaceutically usable salts. Thus, compounds of formula I which carry acidic groups, e.g., one or more COOH groups, for example, as alkali metal salts, preferably sodium or potassium salts, or as alkaline earth metal salts, e.g., calcium or magnesium salts, or as ammonium salts, e.g., as salts with ammonia or organic amines or amino acids, can be used. Compounds of formula I which carry one or more basic, i.e., protonatable, groups or contain one or more basic heterocyclic rings can also be used in the form of their physiologically tolerated acid addition salts with inorganic or organic acids, for example, as hydrochlorides, phosphates, sulfates, methanesulfonates, acetates, lactates, maleates, fumarates, malates, and gluconates. If compounds of formula I simultaneously contain acidic and basic groups in the molecule, internal salts, so-called betaines, are also subjects of the invention, in addition to the salt forms described. Salts can be obtained from compounds of formula I by customary methods, for example, by combination with an acid or base in a solvent or dispersant, or by anion exchange from other salts.

With appropriate substitution, compounds of formula I may be present in stereoisomeric forms. If compounds of formula I contain one or more centers of asymmetry, they can, independently of one another, have the S-configuration or the R-configuration. The invention relates to all possible stereoisomers, e.g., enantiomers or diastereomers, and mixtures of two or more stereoisomeric forms, e.g., enantiomers and/or diastereomers, in any ratio. The invention thus relates to enantiomers, for example, in the form of pure enantiomers, both as levorotatory and dextrorotatory antipodes, and also in the form of mixtures of the two enantiomers in different ratios or in the form of racemates. When cis/trans isomerism is present, the invention relates both to the cis form and to the trans form and mixtures of these forms. The preparation of individual stereoisomers can be carried out, if desired, by separating a mixture by customary methods or, for example, by stereoselective synthesis. When mobile hydrogen atoms are present, the present invention also comprises all tautomeric forms of compounds of formula I.

Compounds of formula I can be prepared by different chemical processes, which likewise form subjects of the present invention. Thus, for example, a compound of formula I is obtained by reacting a carboxylic acid of formula IV,

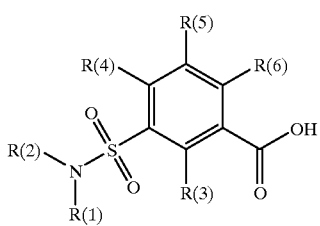

IV in which R(1), R(2), R(3), R(4), R(5), and R(6) have the abovementioned meanings with an amine of formula Va or Vb

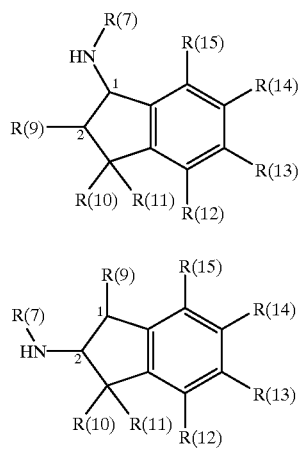

in which R(7), R(9), R(10), R(11), R(12), R(13), R(14), and R(15) have the abovementioned meanings, in a manner known per se, in an amidation reaction.

Numerous methods for carrying out these reactions have been described in the literature. They can be particularly advantageously carried out by activating the carboxylic acid, for example, with dicyclohexylcarbodiimide (DCC), if required with the addition of hydroxybenzotriazole (HOBT) or dimethylaminopyridine (DMAP), or with C)-[(cyano (ethoxycarbonyl)-methylene)amino]-1,1,3,3-tetramethyluronium tetrafluoroborate (TOTU). However, it is also possible first to synthesize reactive acid derivatives by known methods, for example, acid chlorides by reacting carboxylic acids of formula IV with inorganic acid halides, such as, for example, $SOCl_2$, or acid imidazolides by reaction with carbonyldiimidazole, which are then reacted with the amines of formulae Va or Vb, if required with addition of an auxiliary base.

The amines of formulae Va or Vb are either known from the literature or can be prepared analogously to known methods, for example, by reductive amination of the corresponding 1-indanones or by epoxidation of the corresponding 1 H-indenes and subsequent epoxide opening with an amine of formula $R(7)-NH_2$.

The carboxylic acids of formula IV can be obtained, for example, from the chlorosulfonyl compounds of formula VI

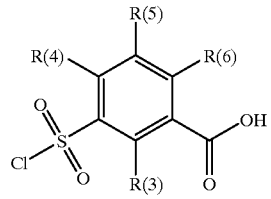

VI by reaction with an amine of formula R(1)R(2)NH in a suitable inert solvent, such as, for example, diethyl ether, THF, or acetone, and, if required, in the presence of an auxiliary base, such as, for example, triethylamine.

Chlorosulfonyl compounds of formula VI are either known from the literature or can be prepared analogously to known methods, for example, by chlorosulfonation or correspondingly substituted benzoic acids with chlorosulfonic acid.

In all procedures, it may be appropriate temporarily to protect functional group.,- in the molecule in specific reaction steps. Such protective group techniques are familiar to a person skilled in the art. The choice of a protective group for suitable groups and the processes for their introduction and elimination are described in the literature and, if required, can be adapted to the specific case without difficulties.

Compounds, according to the invention, of formula I and their physiologically tolerated salts can thus be used as a medicament alone, in mixtures with one another, or in the form of pharmaceutical formulations, in animals, preferably in mammals, and in particular in humans. The present invention also relates to compounds of formula I and their physiologically tolerated salts for use as medicaments, their use in the therapy and prophylaxis of said pathological states, and their use for the preparation of medicaments for this purpose and of medicaments having a $K^+$-channel-blocking effect. Furthermore, the present invention relates to pharmaceutical formulations which contain, as an active ingredient, an effective dose of at least one compound of formula I and/or of one physiologically tolerated salt thereof in addition to customary, pharmaceutically satisfactory carriers and auxiliaries. The pharmaceutical formulations usually contain from 0.1 to 90% by weight of compounds of formula I and/or of their physiologically tolerated salts. The preparation of the pharmaceutical formulations can be carried out in a manner known per se. For this purpose, compounds of formula I and/or their physiologically tolerated salts, together with one or more solid or liquid pharmaceutical carriers and/or auxiliaries and, if desired, in combination with other pharmaceutical active substances, are brought into a suitable administration form or dosage form, which can then be used as a medicament in human medicine or veterinary medicine.

Medicaments which contain compounds, according to the invention, of formula I and/or their physiologically tolerated salts can be administered orally, parenterally, e.g., intravenously, rectally, by inhalation, or topically, the preferred administration depending on the specific case, for example, the respective symptom of the disease to be treated.

Auxiliaries that are suitable for the desired medicament formulation are familiar to the person skilled in the art on the basis of his technical knowledge. In addition to solvents, gel formers, suppository bases, tablet auxiliaries, and other active substance carriers, it is possible to use, for example, antioxidants, dispersants, emulsifiers, antifoams, flavoring agents, preservatives, solubilizers, compositions for achieving a depot effect, buffer substances, or colorants.

Compounds of formula I can also be combined with other pharmaceutical active ingredients in order to achieve an advantageous therapeutic effect. Thus, combinations with substances having cardiovascular activity, which combinations are advantageous in the treatment of cardiovascular diseases, are possible. Suitable combination partners of this type which are advantageous for cardiovascular diseases are, for example, other antiarrhythmic drugs, for example, class I, class II, or class III antiarrhythmic drugs, such as, for example, $IK_s$- or $IK_r$-channel blockers, e.g., dofetilide, or furthermore, hypotensive substances, such as ACE inhibitors (for example, enalapril, captopril, and ramipril), angiotensin antagonists, $K^+$-channel activators, and alpha- and beta-receptor blockers, as well as sympathomimetic and adrenergic compounds, and $NA^+/H^+$ exchange inhibitors, calcium channel antagonists, phosphodiesterase inhibitors, and other substances having positive inotropic activity, such as, for example, digitalis glycosides or diuretics.

For an oral application form, the active compounds are mixed with the additives suitable for this purpose, such as carriers, stabilizers, or inert diluents, and brought by the customary methods into the suitable dosage forms, such as tablets, coated tablets, capsules, or aqueous, alcoholic, or oily solutions. For example, gum arabic, magnesia, magnesium carbonate, potassium phosphate, lactose, glucose, or starch, in particular corn starch, can be used as inert carriers. Formulation may be in the form of both dry granules and moist granules. Suitable oily carriers or suitable solvents are, for example, vegetable or animal oils, such as sunflower oil or cod-liver oil. Suitable solvents for aqueous or alcoholic solutions are, for example, water, ethanol, or sugar solutions or mixtures thereof. Further auxiliaries, also for other application forms are, for example, polyethylene glycols and polypropylene glycols.

For subcutaneous or intravenous application, the active compounds, if desired for the substances customary for this purpose, such as solubilizers, emulsifiers, or further auxiliaries, are brought into solution, suspension, or emulsion. Compounds of formula I and their physiologically tolerated salts may also be lyophilized and the resulting lyophilized products may be used, for example, for the preparation of injection or infusion preparations. Suitable solvents are, for example, water, physiological saline solution, or alcohols, e.g., ethanol, propanol, or glycerol, as well as sugar solutions, such as glucose or mannitol solutions, or mixtures of the various solvents mentioned.

Suitable pharmaceutical formulations for administration in the form of aerosols or sprays are, for example, solutions, suspensions, or emulsions of the active substances of formula I or their physiologically tolerated salts in a pharmaceutically acceptable solvent, such as, in particular, ethanol or water, or a mixture of such solvents. If required, formulation may also contain other pharmaceutical auxiliaries, such as surfactants, emulsifiers, and stabilizers as well as a propellant. Such a formulation contains the active substance usually in a concentration of from about 0.1 to about 10, in particular from about 0.3 to about 3, % by weight.

The dosage of the active substance of formula I to be administered or of the physiologically tolerated salts depends on the specific case and, as usual, should be adapted to the circumstances of the specific case for optimum effect. Thus, it does of[] course depend on the frequency of administration and on the intensity of action and duration of action of the compounds used in each case for therapy or prophylaxis, as well as on the type and intensity of the disease to be treated, and on the sex, age, weight, and individual responsiveness of the human or animal to be treated, and on whether acute or prophylactic treatment is being carried out. Usually, the daily dose of a compound of formula I when administered to a patient weighing about 75 kg is from 0.001 mg/kg body weight to 100 mg/kg body weight, preferably from 0.01 mg/kg body weight to 20 mg/kg body weight. The dose can be administered in the form of a single dose or divided into several, for example, two, three, or four, single doses. Particularly in the treatment of acute cases of cardiac arrhythmias, for example, in an intensive care ward, a parenteral administration by injection or infusion, for example, by a continuous intravenous infusion, may also be advantageous.

EXPERIMENTAL SECTION

List of abbreviations

DMF N,N-dimethylformamide
EA ethyl acetate
m.p. melting point (unless stated otherwise, the melting points of the unpurified crude products are stated; it is quite possible that the melting points of the respective pure substances are substantially higher)
HOBT 1-hydroxy-1 H-benzotriazole
iPr isopropyl
solv solvent
RT room temperature
THF tetrahydrofuran
TOTU O-[(cyano(ethoxycarbonyl)methylene)amino]-1,1,3,3-tetramethyluronium tetrafluoroborate
General method for the synthesis of 3-chlorosulfonylbenzoic acids (formula VI):

0.2 mol of a substituted benzoic acid is introduced into 135 ml of chlorosulfonic acid and the reaction mixture is heated to 120° C. for 4 hours (h). After cooling, it is poured onto 800 g of ice and stirred for 1 h, and the precipitated product is filtered off with suction.

Inter alia, the following 3-chlorosulfonylbenzoic acids were synthesized in this manner:

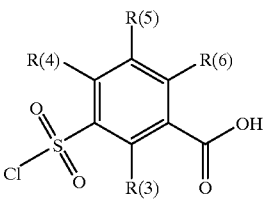

VI

| R(3) | R(4) | R(5) | R(6) | Yield | m.p.(° C.) |
|---|---|---|---|---|---|
| H | Me | H | H | 93% | 174 |
| H | H | H | Cl | 91% | 148 |
| H | H | H | Me | 95% | 151 |
| H | F | H | H | 81% | 140 |
| H | Cl | H | H | 86% | 158 |
| H | Cl | H | Cl | 83% | 185 |
| H | F | H | Cl | 82% | 139 |
| H | Cl | NO$_2$ | Cl | 76% | 235 |
| H | H | NO$_2$ | Cl | 42% | 190 |
| H | Cl | Cl | H | 65% | 207 |
| H | OMe | H | H | 75% | |
| H | H | H | OMe | 80% | 145 |
| H | iPr | H | H | 83% | 192 |
| H | H | Me | Me | 82% | 170 |
| H | Me | H | Me | 88% | 190 |
| H | Me | Me | H | 81% | |

General method for the reaction of 3-chlorosulfonylbenzoic acids (Formula VI) with amines to give sulfonamides of formula IV (Variant A):

10 mmol of the respective 3-chlorosulfonylbenzoic acid are added to a solution of 30 mmol of the corresponding amine in 20 ml of diethyl ether (or methylene chloride) and the reaction mixture is stirred overnight at RT. After the addition of 20 ml of ether (or methylene chloride) and 20 ml of water, the organic phase is extracted twice with dilute hydrochloric acid and then twice with saturated sodium bicarbonate solution. After acidification of the bicarbonate extracts, the product of formula IV is precipitated and is isolated either by filtration with suction or by extraction with EA.

Inter alia, the following sulfonamides of formula IV were synthesized in this manner:

| Structure | m.p.(° C.) | Yield |
|---|---|---|
| 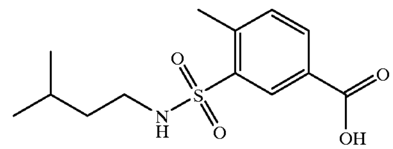 | 154 | 80% |
| 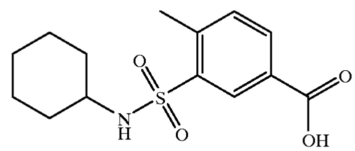 | 179 | 62% |
| 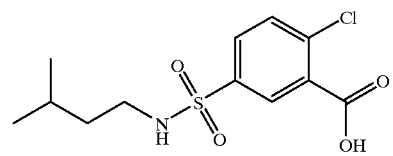 | 162 | 68% |
| 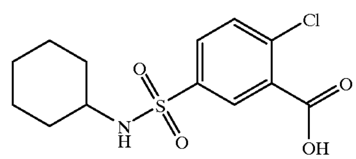 | 182 | 51% |
| 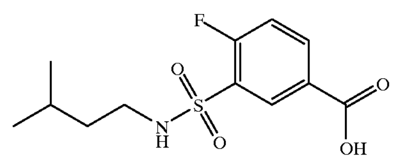 | 141 | 70% |
| 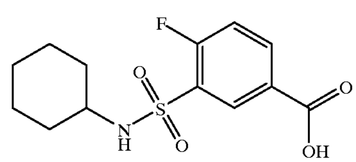 | 170 | 43% |
| 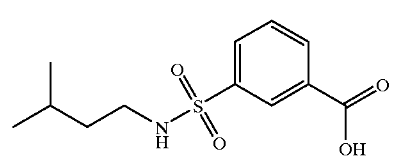 | 197 | 65% |
| 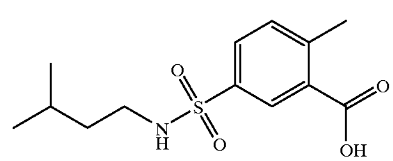 | 192 | 65% |

-continued

| Structure | m.p.(° C.) | Yield |
|---|---|---|
| (cyclohexyl-NH-SO₂-phenyl-COOH, meta) | 204 | 43% |
| (cyclohexyl-NH-SO₂-phenyl(methyl)-COOH) | 220 | 51% |
| (phenyl-NH-SO₂-(dichlorophenyl)-COOH) | 218 | 29% (in acetone as solvent) |
| (phenyl-NH-SO₂-(chlorophenyl)-COOH) | 194 | 81% (in acetone as solvent) |
| (HO-ethyl-phenyl-NH-SO₂-(dichlorophenyl)-COOH) | 183 | 14% (in THF as solvent) |
| (benzyl-NH-SO₂-(chlorophenyl)-COOH) | 201 | |
| (piperidinyl-SO₂-(chlorophenyl)-COOH) | 209 | 36% |

-continued

| Structure | m.p.(° C.) | Yield |
|---|---|---|
| | | 76% |
| | | 87% |

General method for the synthesis of compounds, according to the invention, of formula I from 3-chlorosulfonylbenzoic acids of formula VI (Variant B):

3 mmol of an amine of formula HNR(1)R(2) are dissolved in 20 to 50 ml of diethyl ether, and 1 mmol of 3-chlorosulfonylbenzoic acid (formula VI) dissolved in ether is added. Stirring is carried out for 30 min at RT, the pH is adjusted to 1 with 2 M hydrochloric acid, and the phases are separated. The organic phase is dried, filtered, and evaporated down in vacuo. The residue is refluxed with 5 ml of thionyl chloride for 40 min. Thereafter, the excess thionyl chloride is removed in vacuo, and coevaporation is effected several times with toluene. The product thus obtained is taken up in ether or dichloromethane and added to a solution of 1 mmol of aminoindane (formula II or III) and 1 mmol of Hünig base in ether and stirred for 20 min at RT. Thereafter, the pH is,, adjusted to 1 with 2 M HCl and the phases are separated. The organic phase is dried, filtered, and evaporated down in vacuo. The crude product is purified by flash chromatography.

General method for the synthesis of compounds, according to the invention, of formula I from sulfonamides of formula IV (Variant C):

1 mmol of a compound of formula IV is refluxed with 5 ml of thionyl chloride for 40 min. Thereafter, the excess thionyl chloride is removed in vacuo and coevaporation is effected several times with toluene. The product thus obtained is taken up in ether or dichloromethane and added to a solution of 10 mmol of aminoindane in ether and stirred at RT until the reaction is complete. After the reaction mixture has been evaporated down, the residue is purified by means of preparative HPLC.

General method for the synthesis of compounds, according to the invention, of formula I from sulfonamides of formula IV (Variant D):

From 1.15 to 1.40 mmol of carbonyldiimidazole are added to a solution or suspension of 1 mmol of a compound of formula IV in THF, and the reaction mixture is stirred for 3 h at RT. After the addition of from 1.1 to 1.5 mmol of a 1- or 2-aminoindane of formula Va or Vb, respectively, stirring is carried out overnight at RT and the reaction mixture is then evaporated down in vacuo. The residue is taken up in EA and washed with dilute hydrochloric acid and sodium bicarbonate solution. After the organic phase has been evaporated down in vacuo, the residue is dissolved in isopropanol and the product is precipitated by adding water. After filtration with suction and drying, compounds of formula I are obtained in a purity of >90% (some of them are contaminated with up to 10% of the corresponding bisindanylurea).

General method for the synthesis of compounds, according to the invention, of formula I from sulfonamides of formula IV (Variant E):

1 mmol of a compound of formula IV is reacted with 1 mmol of a 1 - or 2-aminoindane of formula Va or Vb, respectively, in DMF in the presence of 1 mmol of TOTU and 1 mmol of Hünig base. After stirring has been carried out for 2 h at RT, the solvent is removed in vacuo and the crude product is purified by chromatography over RP18 silica gel.

General method for the synthesis of compounds, according to the invention, of formula I from sulfonamides of formula IV (Variant F):

1.55 mmol of a 1- or 2-aminoindane of formula Va or Vb, respectively, are added to a solution of 1.4 mmol of a compound of formula IV, 0.21 g (1.55 mmol) of HOBT, and 0.19 g (1.55 mmol) of diisopropylcarbodiimide in 15 ml of THF at 0° C., and the reaction mixture is stirred overnight at RT. After the precipitate has been filtered off, the filtrate is evaporated down in vacuo and the residue is taken up in EA and is extracted with sodium bicarbonate solution.

Inter alia, the following compounds of formula I were synthesized according to the general methods (Variants B, C, D, E, or F) and are shown in the table below. Compounds for which no melting point is given were isolated as oils or amorphous glassy products. Compounds for which no information on synthesis variant used is shown were obtained analogously to the methods described but with the use of slight variations, such as, for example, different solvents and different coupling reagent. In no case is it absolutely essential to use a specific method, and as a rule all variants can be used.

| Example | Structure | m.p.(° C.) | Method | Yield |
|---|---|---|---|---|
| 1 | 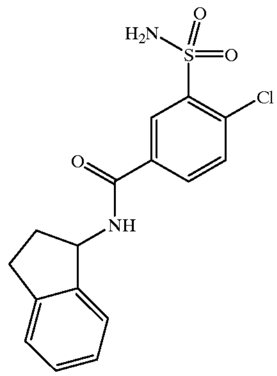 | 210 | | |
| 2 | 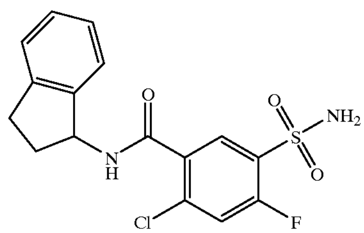 | 217 | | |
| 3 | 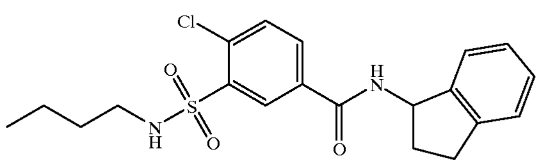 | 139 | | |
| 4 | Chiral | 239 | | |
| 5 | 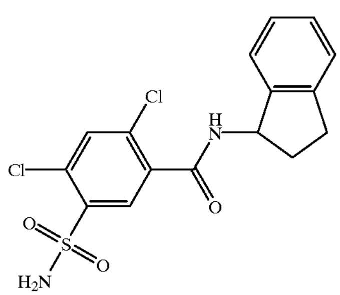 | 248 | | |

-continued
| Example | Structure | m.p.(° C.) | Method | Yield |
|---------|-----------|------------|--------|-------|
| 6 | 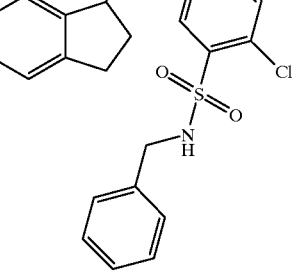 | 177 | | 45% |
| 7 | 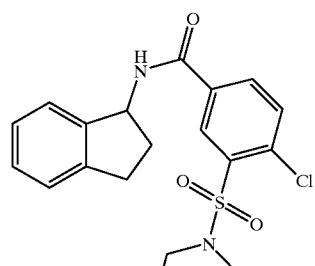 | | | |
| 8 | 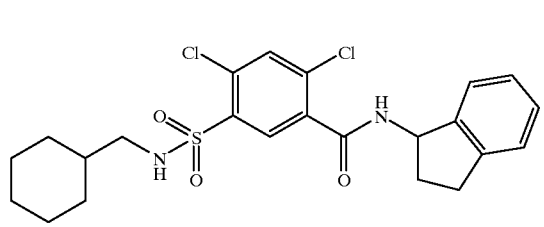 | | B | |
| 9 | 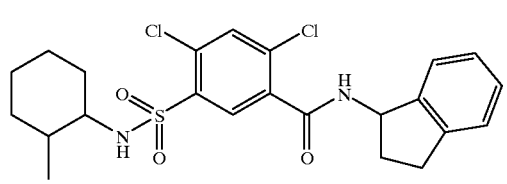 | | B | |
| 10 | 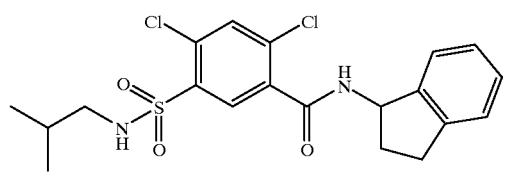 | | B | |
| 11 | 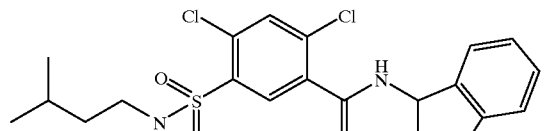 | | B | |

-continued

| Example | Structure | m.p.(° C.) | Method | Yield |
|---|---|---|---|---|
| 12 | 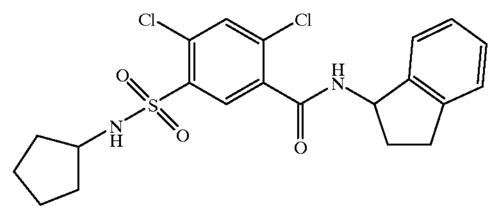 | 82 | C | 54% |
| 13 | 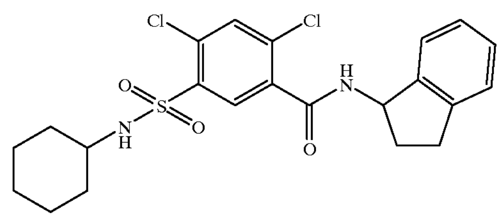 | 71 | B | 66% |
| 14 | 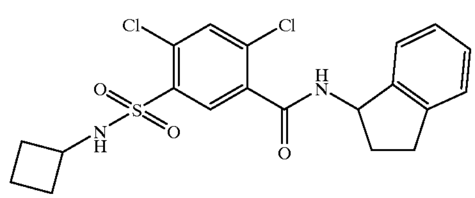 | 86 | C | 14% |
| 15 | 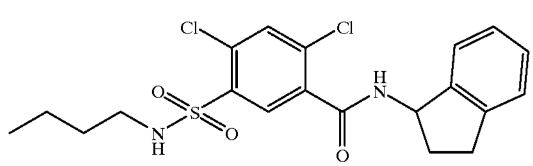 | 71 | C | 74% |
| 16 | 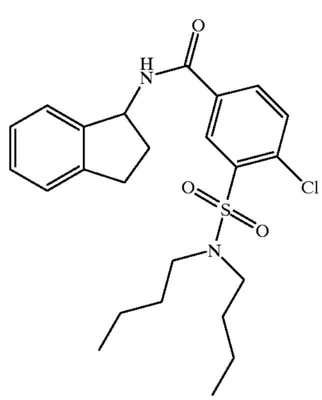 | | | |

-continued

| Example | Structure | m.p.(° C.) | Method | Yield |
|---------|-----------|------------|--------|-------|
| 17 | 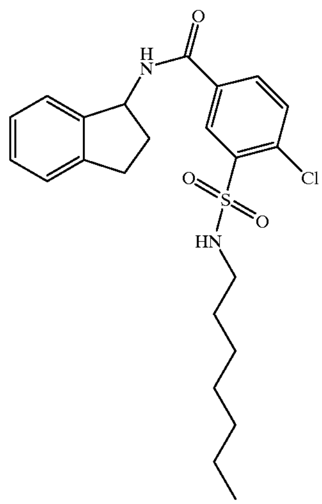 | | | |
| 18 | 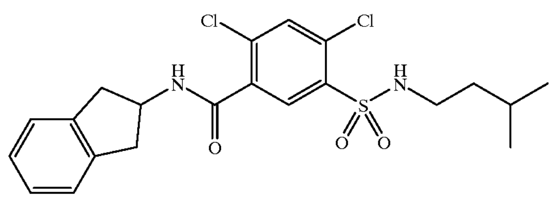 | | | |
| 19 | Chiral | | | |
| 20 | Chiral | | | |
| 21 | 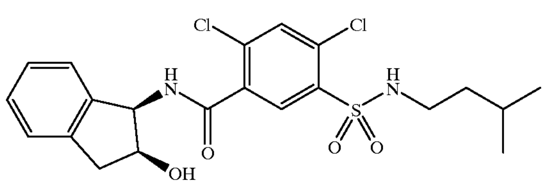 | | | |
| 22 | 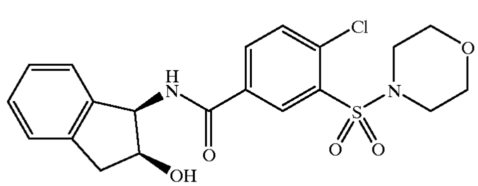 | | | |

-continued

| Example | Structure | m.p.(° C.) | Method | Yield |
|---|---|---|---|---|
| 23 | Chiral | | | |
| 24 | Chiral | 173 | D | 99% |
| 25 | Chiral | 174 | D | 99% |
| 26 | 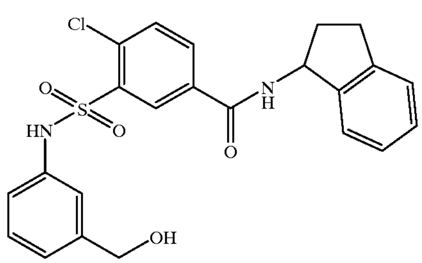 | 89 | E | 38% |

-continued

| Example | Structure | m.p.(° C.) | Method | Yield |
|---|---|---|---|---|
| 27 | 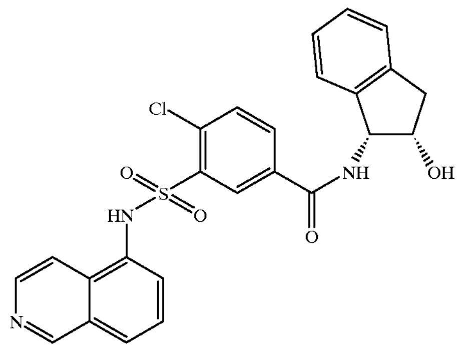 | | E | 28% |
| 28 | 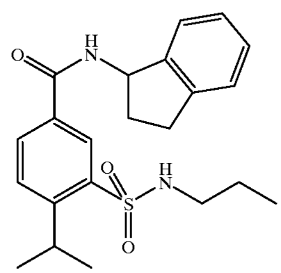 | | D | 99% |
| 29 | 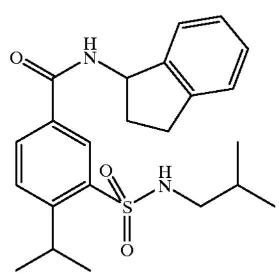 | | D | 99% |
| 30 | 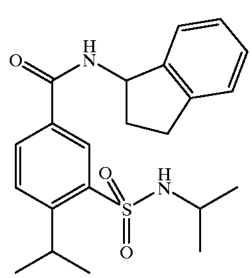 | | D | 99% |
| 31 | 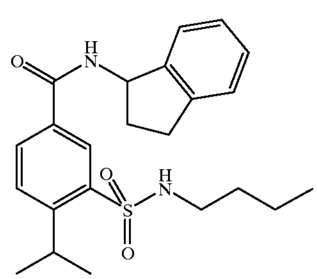 | | D | 99% |

-continued

| Example | Structure | m.p.(° C.) | Method | Yield |
|---|---|---|---|---|
| 32 | 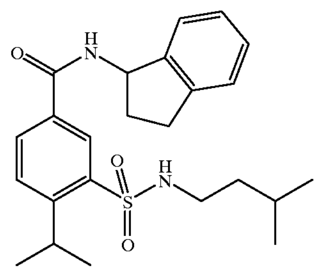 | | D | 99% |
| 33 | 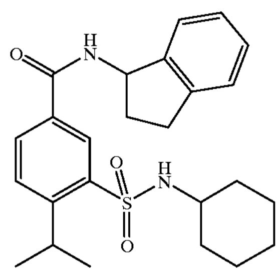 | | D | 99% |
| 34 | 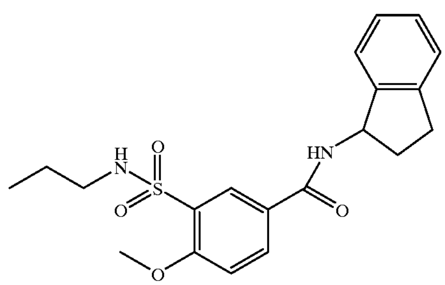 | 168 | D | 99% |
| 35 | 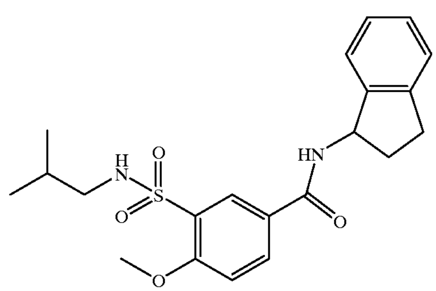 | 186 | D | 99% |
| 36 | 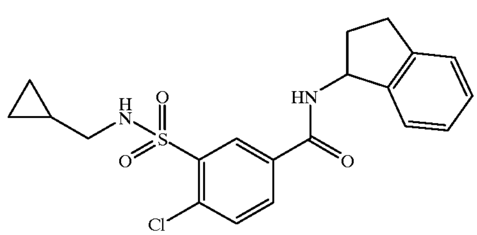 | | | |

-continued

| Example | Structure | m.p.(° C.) | Method | Yield |
|---|---|---|---|---|
| 37 | 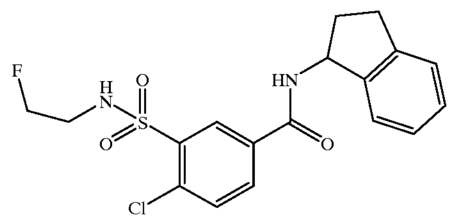 | | | |
| 38 | 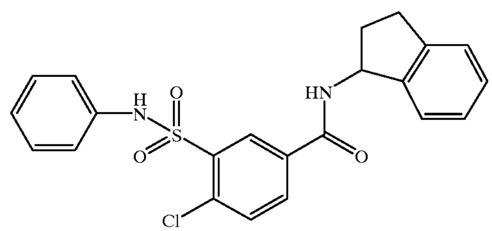 | | | |
| 39 | 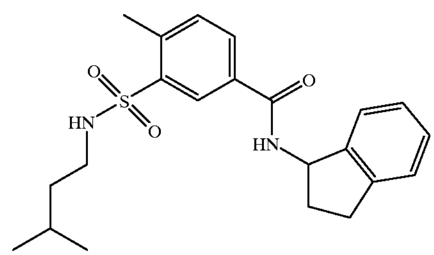 | 139 | D | 84% |
| 40 | 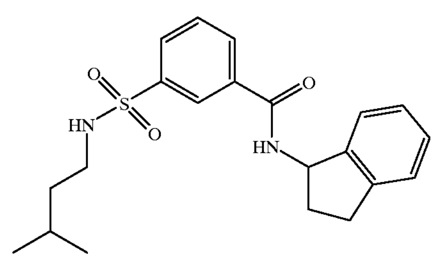 | 136 | D | 75% |
| 41 | 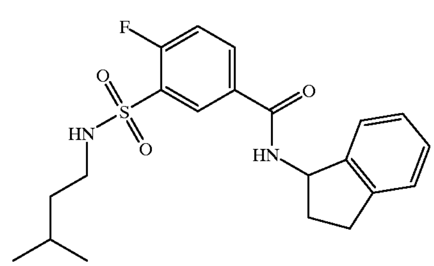 | 145 | D | 80% |
| 42 | 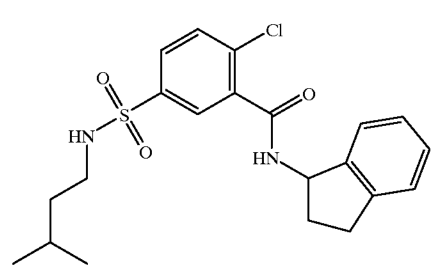 | 110 | D | 79% |

-continued

| Example | Structure | m.p.(° C.) | Method | Yield |
|---|---|---|---|---|
| 43 | 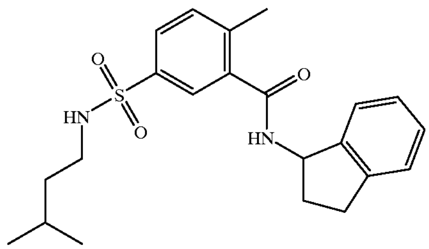 | 114 | D | 70% |
| 44 | 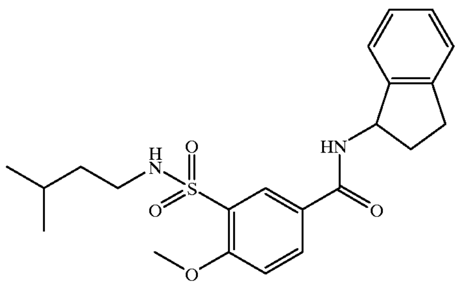 | 70–80 | D | 72% |
| 45 | 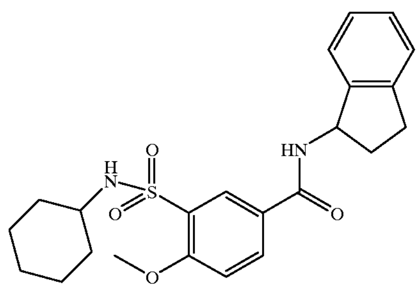 | 193–197 | D | 99% |
| 46 | 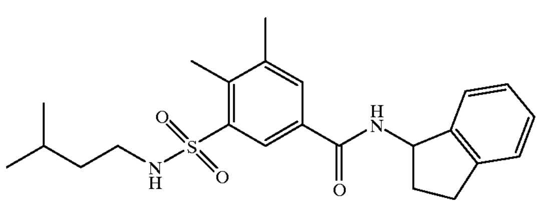 | 196 | E | 34% |
| 47 | 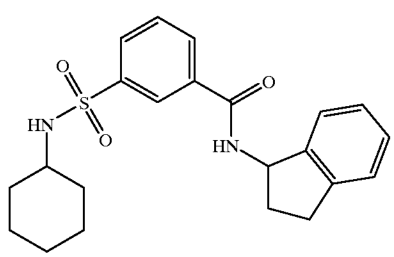 | 154 | D | 26% |

-continued

| Example | Structure | m.p.(° C.) | Method | Yield |
|---------|-----------|------------|--------|-------|
| 48 | 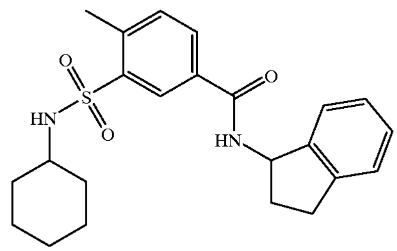 | 185 | D | 45% |
| 49 | 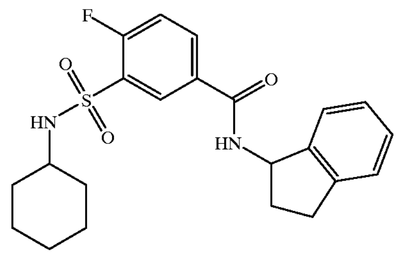 | 176 | D | 75% |
| 50 | 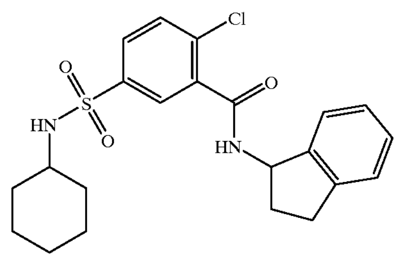 | (glassy) | D | 51% |
| 51 | 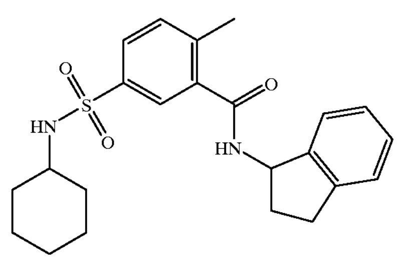 | (glassy) | D | 89% |
| 52 | 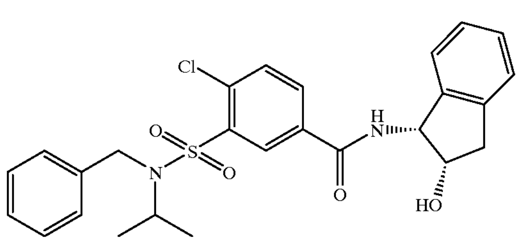 | 141 | E | 44% |

-continued

| Example | Structure | m.p.(° C.) | Method | Yield |
|---|---|---|---|---|
| 53 | 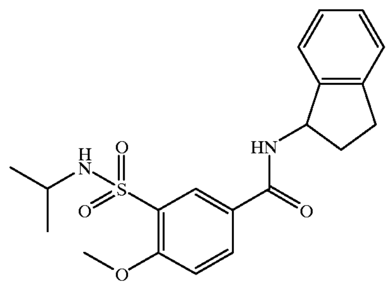 | 183 | D | 85% |
| 54 | 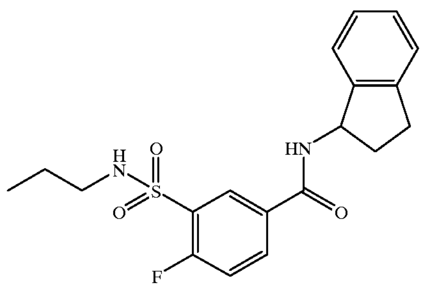 | | D | 90% |
| 55 | 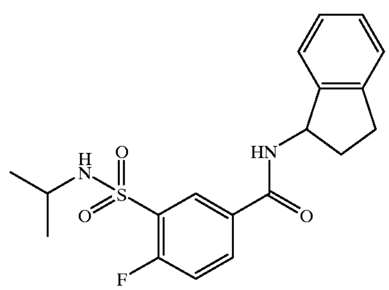 | | D | 98% |
| 56 | 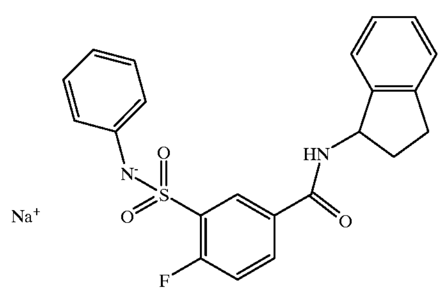 | 225–229 | D | 99% |
| 57 | 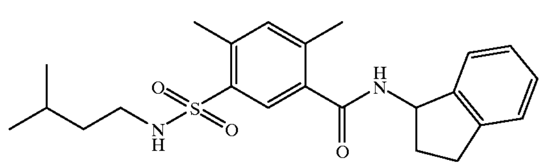 | | E | 61% |

-continued

| Example | Structure | m.p.(° C.) | Method | Yield |
|---|---|---|---|---|
| 58 | 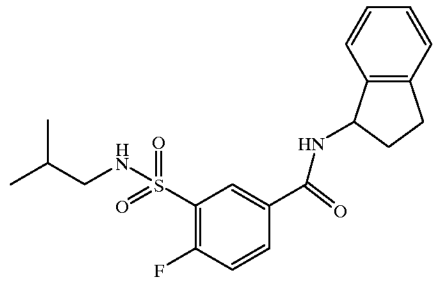 | | D | 62% |
| 59 | 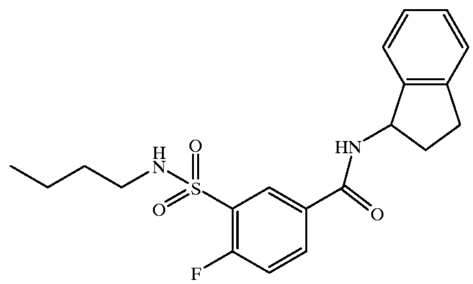 | 133 | D | 90% |
| 60 | 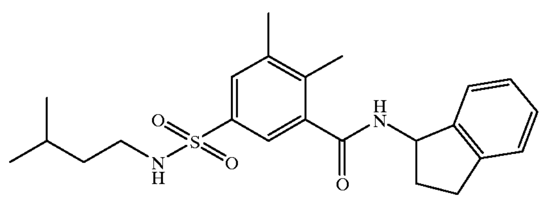 | 144 | E | 79% |
| 61 | 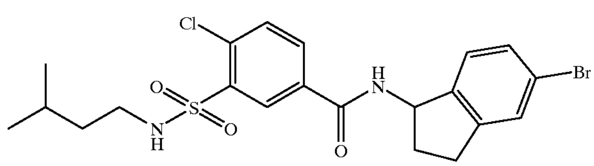 | 108 | E | 49% |
| 62 | 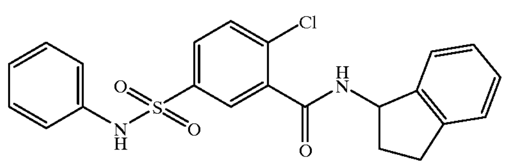 | 140 | F | 54% |
| 63 | 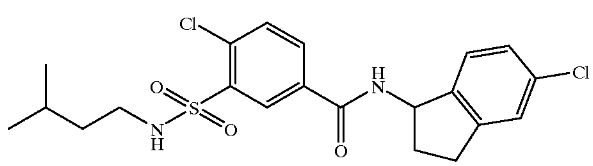 | 69 | E | 24% |
| 64 | 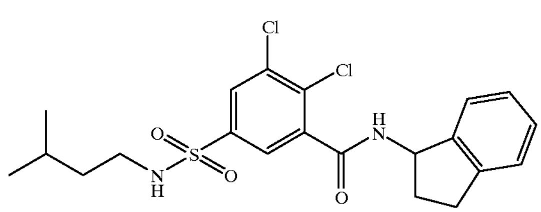 | | E | |

-continued

| Example | Structure | m.p.(° C.) | Method | Yield |
|---|---|---|---|---|
| 65 | 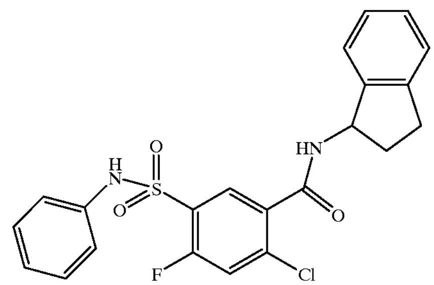 | | D | |
| 66 | 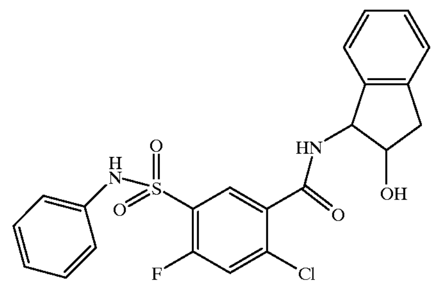 | | D | |
| 67 | 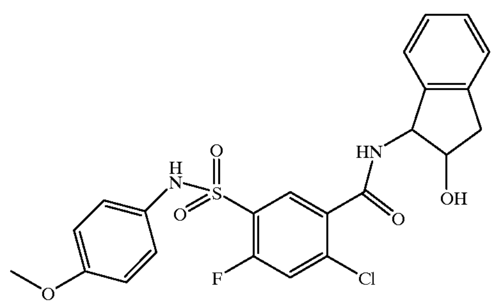 | | D | |
| 68 | 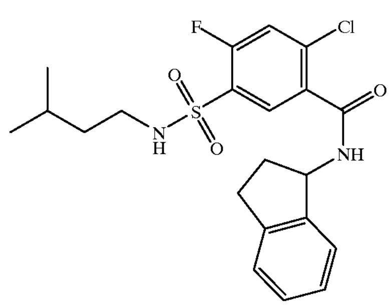 | 145 | F | 88% |
| 69 | 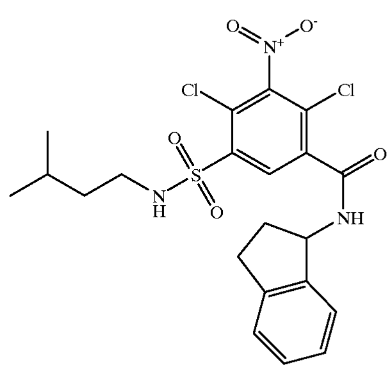 | 165 | F | 84% |

-continued
| Example | Structure | m.p.(° C.) | Method | Yield |
|---|---|---|---|---|
| 70 | 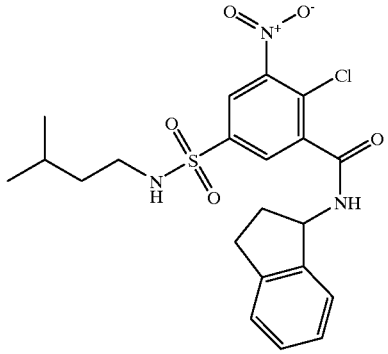 | 168 | F | 86% |
| 71 | 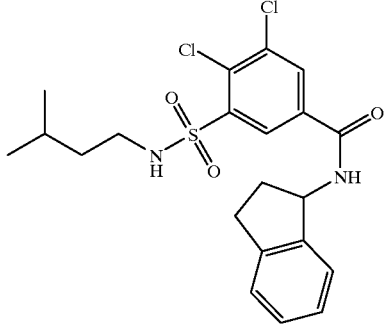 | 127 | F | 81% |
| 72 | 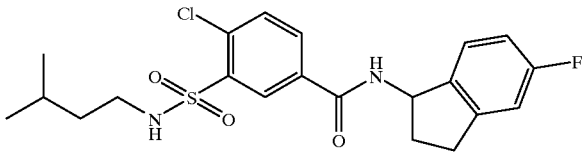 | | E | |
| 73 | 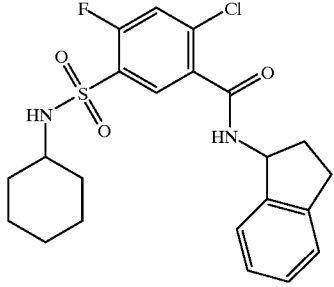 | 164 | F | 63% |

-continued

| Example | Structure | m.p.(° C.) | Method | Yield |
|---|---|---|---|---|
| 74 | 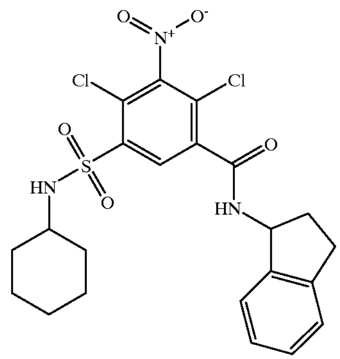 | 201 | F | 28% |
| 75 | 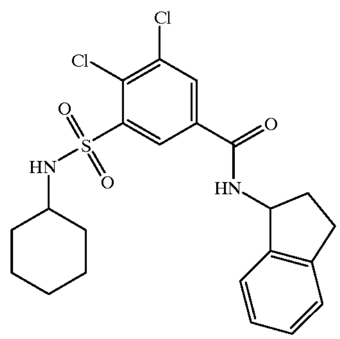 | | F | 63% |
| 76 | Chiral | | F | 42% |
| 77 | Chiral | | F | 25% |

-continued
| Example | Structure | m.p.(° C.) | Method | Yield |
|---|---|---|---|---|
| 78 | 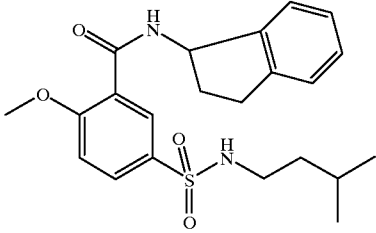 | | D | |
| 79 | 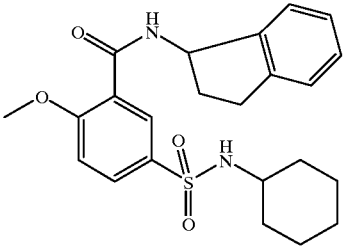 | | D | |
| 80 | 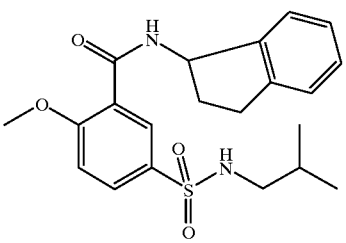 | | D | |
| 81 | 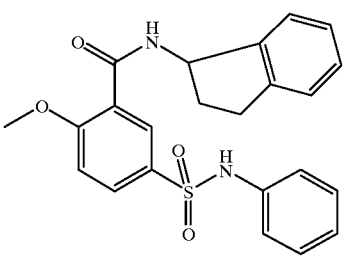 | | D | |
| 82 | 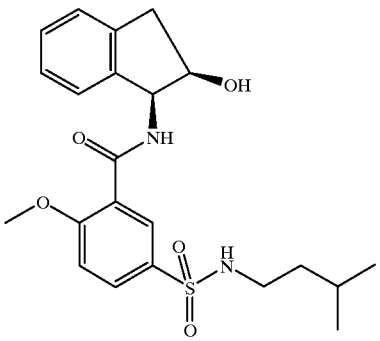 | | D | |

-continued

| Example | Structure | m.p.(° C.) | Method | Yield |
|---|---|---|---|---|
| 83 | 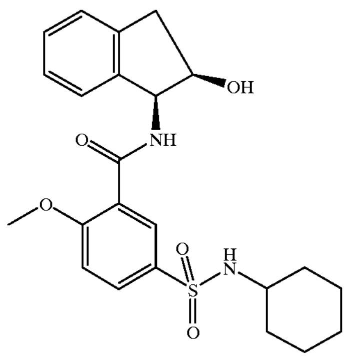 | | D | |
| 84 | 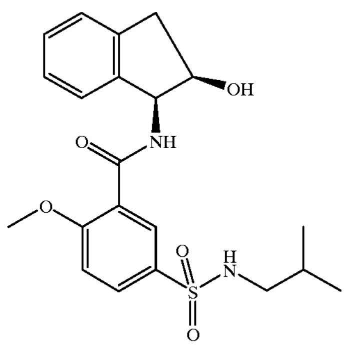 | | D | |
| 85 | 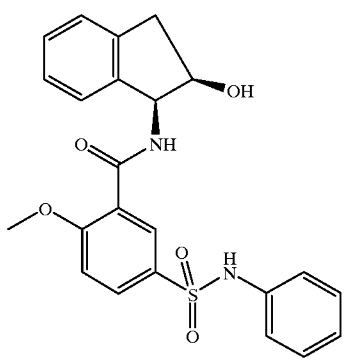 | | D | |
| 86 | 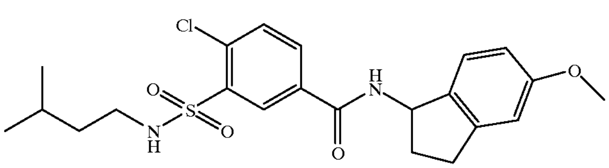 | | E | |
| 87 | 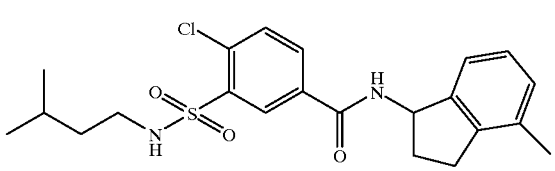 | | E | |

-continued

| Example | Structure | m.p.(° C.) | Method | Yield |
|---|---|---|---|---|
| 88 | 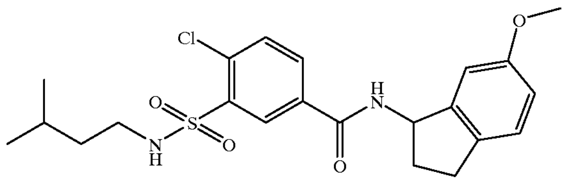 | | E | |
| 89 | 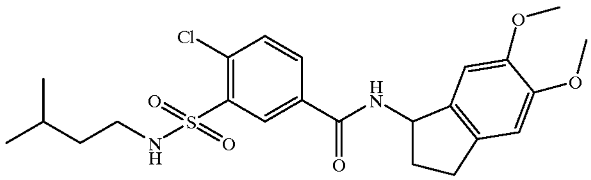 | | E | |
| 90 | 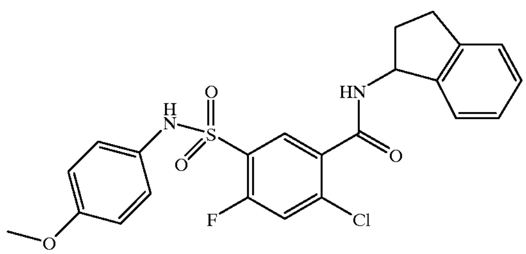 | 155 | D | |
| 91 | 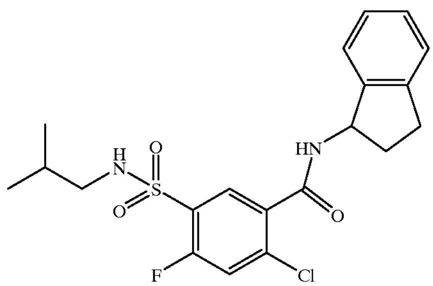 | 153 | D | |
| 92 | 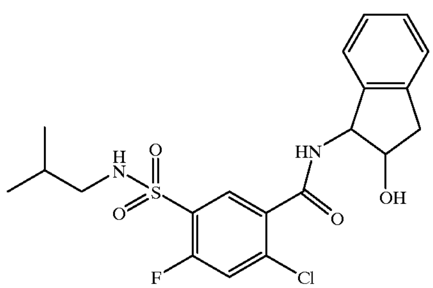 | 182 | D | |
| 93 | 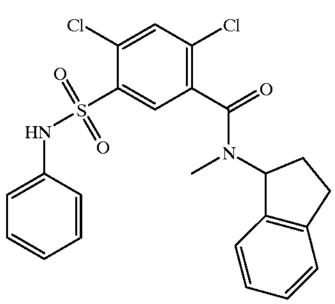 | 114 | F | 37% |

-continued

| Example | Structure | m.p.(° C.) | Method | Yield |
|---|---|---|---|---|
| 94 | 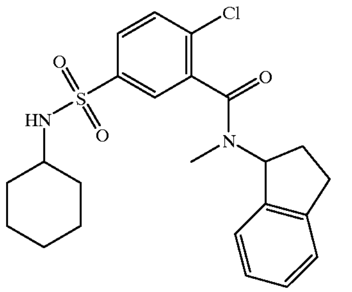 | | F | 50% |
| 95 | 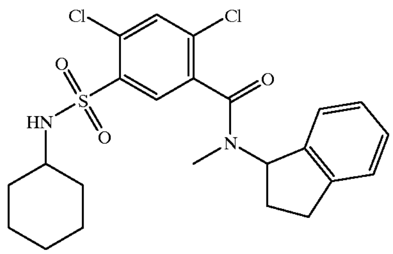 | 183 | F | 37% |
| 96 | 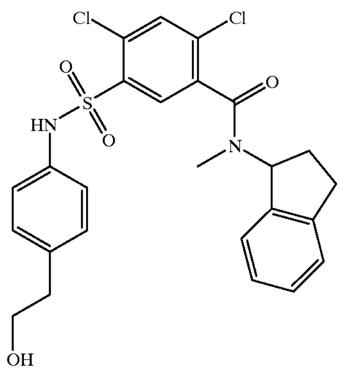 | | F | 6% |

EXAMPLE 97:

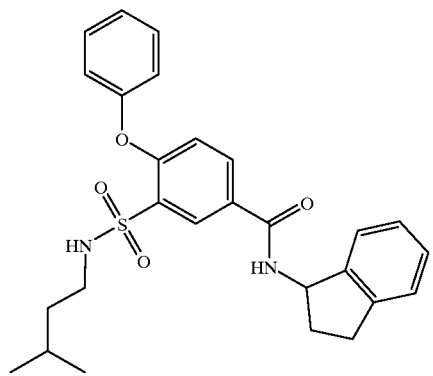

A solution of 100 mg of 4-fluoro-N-indan-1-yl-3-(3-methyl-butylsulfamoyl)benzamide (Example 41), 26 mg of phenol, and 100 mg of potassium carbonate in 4 ml of N,N-dimethylacetamide was heated to 100° C. for 6 h. After water had been added and the precipitated product filtered off with suction, 82 mg of 4-phenoxy-N-indan-1-yl-3-(3-methyl-butylsulfamoyl)benzamide were obtained; m.p. 73° C.

EXAMPLE 98:

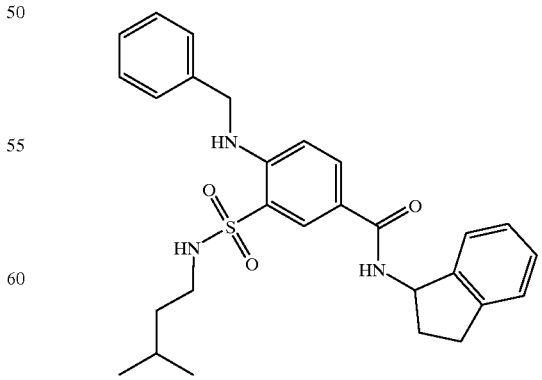

A solution of 100 mg of 4-fluoro-N-indan-1-yl-3-(3-methylbutylsulfamoyl)benzamide (Example 41), 29 mg of benzylamine, and 100 mg of potassium carbonate in 4 ml of N,N-dimethylacetamide was heated to 100° C. for 6 h. After the addition of water, extraction with EA, and chromatographic separation, 33 mg of 4-benzylamino-N-indan-1-yl-3-(3-methylbutylsulfamoyl)benzamide were obtained.

EXAMPLE 99:

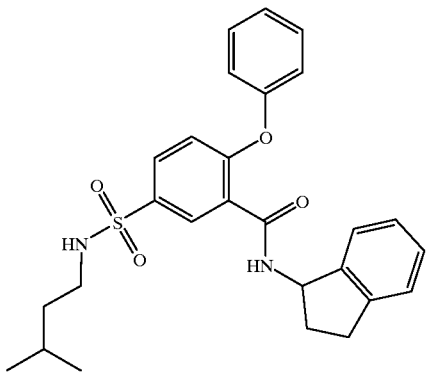

75 mg of 2-phenoxy-N-indan-1-yl-5-(3-methylbutylsulfamoyl)benzamide were obtained from 100 mg of 2-chloro-N-indan-1-yl-5-(3-methylbutylsulfamoyl)benzamide (Example 42) analogously to Example 97.

Pharmacological Investigations

Human Kv1.5 channels were expressed in Xenopus oocytes. For this purpose, oocytes were first isolated from *Xenopus laevis* and were defolliculated. Kv1.5-coding RNA synthesized in vitro was then injected into these oocytes. After Kv1.5 protein expression for 1-7 days, Kv1.5 currents were measured on the oocytes by the two microelectrode voltage clamp technique. Here, the Kv1.5 channels were activated as a rule with voltage jumps to 0 mV and 40 mV, lasting for 500 ms. The bath was flushed with a solution of the following composition: 96 mM NACl, 2 mM KCl, 1.8 mM $CaCl_2$, 1 mM $MgCl_2$, and 5 mM HEPES (tritrated with NaOH to pH 7.4). These experiments were carried out at RT. The following were used for data acquisition and analysis: Geneclamp amplifier (Axon Instruments, Foster City, USA) and MacLab D/A converter and software (ADinstruments, Castle Hill, Australia). The substances according to the invention were tested by adding them in different concentrations to the bath solution. The effects of the substances were calculated as percentage inhibition of the Kv1.5 control current obtained when no substance was added to the solution. The data were then extrapolated using the Hill equation, in order to determine the inhibitory concentration ($IC_{50}$) for the respective substances.

In this way, the following $IC_{50}$ values were determined for the compounds listed below:

| Compound | $IC_{50}$ ($\mu$M) |
| --- | --- |
| Example 1 | >>10 |
| Example 3 | 7.7 |
| Example 10 | 4.8 |
| Example 11 | 2.8 |
| Example 13 | 3.9 |
| Example 14 | 4.2 |
| Example 19 | ~3 |

-continued

| Compound | $IC_{50}$ ($\mu$M) |
| --- | --- |
| Example 20 | ~3 |
| Example 43 | 5.3 |
| Example 51 | 7.1 |
| Example 57 | 8.8 |
| Example 60 | 6.9 |
| Example 62 | 6.3 |
| Example 73 | 6.2 |
| Example 88 | 8.7 |
| Example 89 | 5.6 |
| Example 90 | 2.8 |
| Example 94 | 2.2 |

The present invention may be embodied in other specific forms without departing from its spirit or essential characteristics. The described embodiments are lo be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A compound of formula I

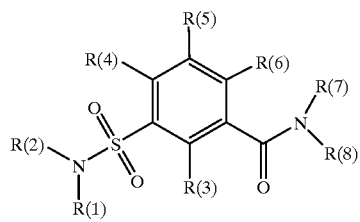

in which R(8) is either a 1-indanyl radical of formula II or a 2-indanyl radical of formula III

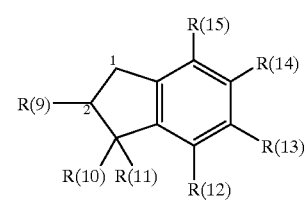

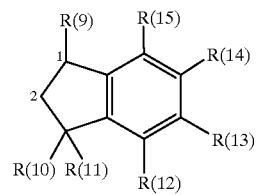

and in which:

R(1) and R(2), independently of one another, are R(20)-$C_rH_{2r}$, where at least one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(21)—, or —CONR(21);

R(21) is hydrogen or alkyl having 1, 2, or 3 carbon atoms;

R(20) is H, CH$_3$, CH$_2$F, CHF$_2$, CF$_3$, C$_2$F$_5$, C$_3$F$_7$, cycloalkyl having 3, 4, 5, 6, 7, or 8 carbon atoms, NR(22)R(23), —CONR(22)R(23), —OR(24), —COOR(24), phenyl, or an N-containing heterocycle having 1, 2, 3, 4, .5, 6, 7, 8, or 9 carbon atoms,
  where phenyl and the N-containing heterocycle are unsubstituted or substituted by 1 or 2 substituents selected from F, Cl, Br, I, CF$_3$, NO$_2$, CN, NH$_2$, OH, methyl, ethyl, hydroxy-methyl, hydroxyethyl, methoxy, dimethylamino, sulfamoyl, methylsulfonyl, and methylsulfonylamino;
R(22) and R(23), independently of one another, are hydrogen or alkyl having 1, 2, 3, or 4 carbon atoms;
or
  R(22) and R(23) together form a chain of 4 or 5 methylene groups, of which one CH$_2$ group is optionally replaced by —O—, —S—, —NH—, —N(methyl)—, or —N(benzyl)—;
  R(24) is hydrogen or alkyl having 1, 2, or 3 carbon atoms;
r is 0, 1, 2, 3, 4, 5, 6, 7, or 8;
or
R(1) and R(2) together form a chain of 4 or 5 methylene groups, of which one CH$_2$ group is optionally replaced by —O—, —S—, —NH—, —N(methyl)—, or —N(benzyl)—;
R(3), R(4), R(5), and R(6), independently of one another, are hydrogen, F, Cl, Br, I, alkyl having 1, 2, 3, 4, or 5 carbon atoms, cycloalkyl having 3, 4, 5, 6, 7, or 8 carbon atoms, CN, CF$_3$, NO$_2$, OR(25), or NR(26)R(27);
  R(25) is hydrogen, alkyl having 1, 2, 3, or 4 carbon atoms, a fluorinated alkyl radical of formula —C$_x$H$_{2x}$CF$_y$H$_{3-y}$, or phenyl,
    in which phenyl is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methyl-sulfonyl, and methylsulfonylamino;
    x is 0, 1, 2, or 3;
    y is 1, 2, or 3;
  R(26) and R(27), independently of one another, are hydrogen or alkyl having 1, 2, 3, or 4 carbon atoms;
or
  R(26) and R(27) together form a chain of 4 or 5 methylene groups, of which one CH$_2$ group is optionally replaced by —O—, —S—, —NH—, —N(methyl)—, or —N(benzyl)—;
R(7) is hydrogen or alkyl having 1, 2, 3, or 4 carbon atoms;
R(9) is hydrogen, OR(28), or OCOR(28);
  R(28) is hydrogen or alkyl having 1, 2, 3, or 4 carbon atoms;
R(10) and R(11), independently of one another, are hydrogen or alkyl having 1, 2, 3, or 4 carbon atoms;
R(12), R(13), R(14), and R(15), independently of one another, are hydrogen, F, Cl, Br, I, alkyl having 1, 2, 3, 4, or 5 carbon atoms, cycloalkyl having 3, 4, 5, 6, 7, or 8 carbon atoms, —CN, —CF$_3$, —C$_2$F$_5$, —C$_3$F$_7$, —N$_3$, —NO$_2$, —Y—C$_s$H$_{2s}$—R(29), phenyl, thienyl, furyl, or an N-containing heterocycle having 1, 2, 3, 4, 5, 6, 7, 8, or 9 carbon atoms,
  where phenyl, thienyl, furyl, and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamine, sulfamoyl, methylsulfonyl, and methylsulfonylamino;

Y is —O—, —CO—, —CO—O—, —O—CO—, —S—, —SO—, —SO$_2$—, —O—SO$_2$—, —SO$_2$NR(30)-, —CONR(30)—, or —NR(30)CO—, where the link to the backbone is in each case via the atom on the left;
  R(30) is hydrogen or alkyl having 1, 2, or 3 carbon atoms;
s is 0, 1, 2, 3, 4, 5, or 6;
R(29) is hydrogen, methyl, CF$_3$, C$_2$F$_5$, C$_3$F$_7$, cycloalkyl having 3, 4, 5, 6, 7, or 8 carbon atoms, —OR(31), —COOR(31), —NR(32)R(33), —CONR(32)R(33), phenyl, or an N-containing heterocycle having 1, 2, 3, 4, 5, 6, 7, 8, or 9 carbon atoms,
  where phenyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino;
  R(31) is hydrogen or alkyl having 1, 2, or 3 carbon atoms;
  R(32) and R(33), independently of one another, are hydrogen or alkyl having 1, 2, 3, or 4 carbon atoms;
or
  R(32) and R(33) together form a chain of 4 or 5 methylene groups, of which one CH$_2$ group is optionally replaced by —O—, —S—, —NH—, —N(CH$_3$)—, or —N(benzyl)—;
or a physiologically tolerated salt thereof.

2. A compound of claim 1, in which at least one of the radicals R(1) and R(2) is not hydrogen.

3. A compound of claim 1, in which R(8) is either a 1-indanyl radical of formula II or a 2-indanyl radical of formula III and in which:
R(1) is hydrogen;
R(2) is R(20)—C$_r$H$_{2r}$,
  where at least one CH$_2$ group of the group C$_r$H$_{2r}$ is optionally replaced by —O—, —CH=CH—, —C≡C—, —Co—, —CO—O—, —O—CO—, —S—, —SO—, —SO$_2$—, —NR(21)—, or —CONR(21);
  R(21) is hydrogen or alkyl having 1, 2, or 3 carbon atoms;
R(20) is CH$_3$, CH$_2$F, CHF$_2$, CF$_3$, C$_2$F$_6$, C$_3$F$_7$, cycloalkyl having 3, 4, 5, 6, 7, or 8 carbon atoms, NR(22)R(23), —CONR(22)R(23), —OR(24), —COOR(24), phenyl, or an N-containing heterocycle having 1, 2, 3, 4, 5, 6, 7, 8, or 9 carbon atoms,
  where phenyl and the N-containing heterocycle are unsubstituted or substituted by 1 or 2 substituents selected from F, Cl, Br, I, CF$_3$, NO$_2$, CN, NH$_2$, OH, methyl, ethyl, hydroxy-methyl, hydroxyethyl, methoxy, dimethylamino, sulfamoyl, methylsulfonyl, and methylsulfonylamino;
R(22) and R(23), independently of one another, are hydrogen or alkyl having 1, 2, 3, or 4 carbon atoms;
or
  R(22) and R(23) together form a chain of 4 or 5 methylene groups, of which one CH$_2$ group is optionally replaced by —O—, —S—, —NH—, —N(methyl).—, or —N(benzyl)—;
  R(24) is hydrogen or alkyl having 1, 2, or 3 carbon atoms;
r is 0, 1, 2, 3, 4, 5, 6, 7, or 8;
R(3), R(4), R(5), and R(6), independently of one another, are hydrogen, F, Cl, Br, I, alkyl having 1, 2, 3, 4, or 5 carbon atoms, cycloalkyl having 3, 4, 5, 6, 7, or 8 carbon atoms, CN, CF$_3$, NO$_2$, OR(25), or NR(26)R(27);

R(25) is hydrogen, alkyl having 1, 2, 3, or 4 carbon atoms, a fluorinated alkyl radical of formula —$C_xH_{2x}CF_yH_{3-y}$, or phenyl,
in which phenyl is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methyl-sulfonyl, and methylsulfonylamino;
x is 0, 1, 2, or 3;
y is 1, 2, or 3;

R(26) and R(27), independently of one another, are hydrogen or alkyl having 1, 2, 3, or 4 carbon atoms;
or
R(26) and R(27) together form a chain of 4 or 5 methylene groups, of which one $CH_2$ group is optionally replaced by —O—, —S—, —NH—, —N(methyl)—, or —N(benzyl)—;

R(7) is hydrogen or alkyl having 1, 2, 3, or 4 carbon atoms;
R(9) is hydrogen, OR(28), or OCOR(28);
R(28) is hydrogen or alkyl having 1, 2, 3, or 4 carbon atoms;
R(10) and R(11), independently of one another, are hydrogen or alkyl having 1, 2, 3, or 4 carbon atoms;
R(12), R(13), R(14), and R(15), independently of one another, are hydrogen, F, Cl, Br, I, alkyl having 1, 2, 3, 4, or 5 carbon atoms, cycloalkyl having 3, 4, 5, 6, 7, or 8 carbon atoms, —CN, —$CF_3$, —$C_2F_5$, —$C_3F_7$, —$N_3$, —$NO_2$, —Y—$C_sH_{2s}$—R(29), phenyl, thienyl, furyl, or an N-containing heterocycle having 1, 2, 3, 4, 5, 6, 7, 8, or 9 carbon atoms,
where phenyl, thienyl, furyl, and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;

Y is —O—, —CO—, —CO—O—, —O—CO—, —S—, —SO—, —$SO_2$—, —O—$SO_2$—, —$SO_2$NR(30)—, —CONR(30)—, or —NR(30)CO—, where the link to the backbone is in each case via the atom on the left;
R(30) is hydrogen or alkyl having 1, 2, or 3 carbon atoms;
s is 0, 1, 2, 3, 4, 5, or 6;
R(29) is hydrogen, methyl, $CF_3$, $C_2F_5$, $C_3F_7$, cycloalkyl having 3, 4, 5, 6, 7, or 8 carbon atoms, —OR(31), —COOR(31), —NR(32)R(33), —CONR(32)R(33), phenyl, or an N-containing heterocycle having 1, 2, 3, 4, 5, 6, 7, 8, or carbon atoms,
where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;
R(31) is hydrogen or alkyl having 1, 2, or 3 carbon atoms;
R(32) and R(33), independently of one another, are hydrogen or alkyl having 1, 2, 3, or 4 carbon atoms;
or
R(32) and R(33) together form a chain of 4 or 5 methylene groups, of which one $CH_2$ group is optionally replaced by —O—, —S—, —NH—, —N($CH_3$)—, or —N(benzyl)—.

4. A compound of claim 1, in which R(8) is a 1-indanyl radical of formula II and is defined by formula Ia as follows

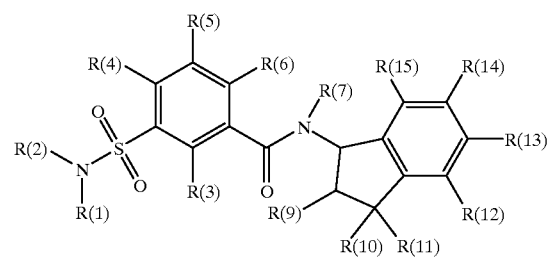

in which:
R(1) is hydrogen;
R(2) is R(20)—$CY_rH_{2r}$, where at least one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(21)—, or —CONR(21);
R(21) is hydrogen or alkyl having 1, 2, or 3 carbon atoms;
R(20) is $CH_3$, $CH_2F$, $CHF_2$, $CF_3$, $C_2F_5$, $C_3F_7$, cycloalkyl having 3, 4, 5, 6, 7, or 8 carbon atoms, NR(22)R(23), —CONR(22)R(23), —OR(24), —COOR(24), phenyl, or an N-containing heterocycle having 1, 2, 3, 4, 5, 6, 7, 8, or 9 carbon atoms,
where phenyl and the N-containing heterocycle are unsubstituted or substituted by 1 or 2 substituents selected from F, Cl, Br, I, $CF_3$, $NO_2$, CN, $NH_2$, OH, methyl, ethyl, hydroxy-methyl, hydroxyethyl, methoxy, dimethylamino, sulfamoyl, methylsulfonyl, and methylsulfonylamino;
R(22) and R(23), independently of one another, are hydrogen or alkyl having 1, 2, 3, or 4 carbon atoms;
or
R(22) and R(23) together form a chain of 4 or 5 methylene groups, of which one $CH_2$ group is optionally replaced by —O—, —S—, —NH—, —N(methyl)—, or —N(benzyl)—;
R(24) is hydrogen or alkyl having 1, 2, or 3 carbon atoms;
r is 0, 1, 2, 3, 4, or 5;
R(3), R(4), R(5), and R(6), independently of one another, are hydrogen, F, Cl, Br, I, alkyl having 1, 2, 3, 4, or 5 carbon atoms, cycloalkyl having 3, 4, 5, 6, 7, or 8 carbon atoms, CN, $CF_3$, $NO_2$, or OR(25);
R(25) is hydrogen, alkyl having 1, 2, 3, or 4 carbon atoms, a fluorinated alkyl radical of formula —$C_xH_{2x}CF_yH_{3-y}$, or phenyl,
in which phenyl is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;
x is 0, 1, 2, or 3;
y is 1, 2, or 3;
R(7) is hydrogen or alkyl having 1, 2, 3, or 4 carbon atoms;
R(9) is hydrogen, OR(28), or OCOR(28);
R(28) is hydrogen or alkyl having 1, 2, 3, or 4 carbon atoms;
R(10) and R(11), independently of one another, are hydrogen or alkyl having 1, 2, 3, or 4 carbon atoms;
R(12), R(13), R(14), and R(15), independently of one another, are hydrogen, F, Cl, Br, I, alkyl having 1, 2, 3, 4, or 5 carbon atoms, cycloalkyl having 3, 4, 5, 6, 7, or 8 carbon atoms, —CN, —CF$_3$, —C$_2$F$_5$, —C$_3$F$_7$, —NO$_2$, —Y—C$_s$H$_{2s}$—R(29), phenyl, thienyl, furyl, or an N-containing heterocycle having 1, 2, 3, 4, 5, 6, 7, 8, or 9 carbon atoms, where phenyl, thienyl, furyl, and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino;

Y is —O—, —CO—, —CO—O—, —O—CO—, —S—, —SO—, —SO$_2$—, —O—SO$_2$—, —SO$_2$NR(30)—, —CONR(30)—, or —NR(30)CO—, where the link to the backbone is in each case via the atom on the left;

R(30) is hydrogen or alkyl having 1, 2, or 3 carbon atoms;

s is 0, 1, 2, 3, 4, 5, or 6;

R(29) is hydrogen, methyl, CF$_3$, C$_2$F$_5$, C$_3$F$_7$, cycloalkyl having 3, 4, 5, 6, 7, or 8 carbon atoms, —OR(31), —COOR(31), —NR(32)R(33), —CONR(32)R(33), phenyl, or an N-containing heterocycle having 1, 2, 3, 4, 5, 6, 7, 8, or 9 carbon atoms, where phenyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonyl-.amino;

R(31) is hydrogen or alkyl having 1, 2, or 3 carbon atoms;

R(32) and R(33), independently of one another, are hydrogen or alkyl having 1, 2, 3, or 4 carbon atoms; or R(32) and R(33) together form a chain of 4 or 5 methylene groups, of which one CH$_2$ group is optionally replaced by —O—, —S—, —NH—, —N(CH$_3$)—, or —N(benzyl)—.

5. A compound of formula Ia of claim 4, in which:

R(1) is hydrogen;

R(2) is R(20)—C$_r$H$_{2r}$;

R(20) is CH$_3$, CH$_2$F, CHF$_2$, CF$_3$, cycloalkyl having 3, 4, 5, 6, 7, or 8 carbon atoms, —CONR(22)R(23), —OR(24), —COOR(24), or phenyl, where phenyl is unsubstituted or substituted by 1 or 2 substituents selected from F, Cl, Br, CF$_3$, NO$_2$, CN, OH, methyl, ethyl, hydroxymethyl, hydroxyethyl, methoxy, dimethylamino, sulfamoyl, methylsulfonyl, and methylsulfonylamino;

R(22) and R(23), independently of one another, are hydrogen or alkyl having 1, 2, 3, or 4 carbon atoms; or R(22) and R(23) together form a chain of 4 or 5 methylene groups, of which one CH$_2$ group is optionally replaced by —O—, —S—, —NH—, —N(methyl)—, or —N(benzyl)—;

R(24) is hydrogen or alkyl having 1, 2, or 3 carbon atoms;

r is 0, 1, 2, 3, 4, or 5;

R(3), R(4), R(5), and R(6), independently of one another, are hydrogen, F, Cl, Br, I, alkyl having 1, 2, 3, 4, or 5 carbon atoms, cycloalkyl having 3, 4, 5, 6, 7, or 8 carbon atoms, CN, CF$_3$, NO$_2$, or OR(25);

R(25) is hydrogen, alkyl having 1, 2, 3, or 4 carbon atoms, a fluorinated alkyl radical of formula —C$_x$H$_{2x}$CF$_y$H$_{3-y}$, or phenyl, in which phenyl is unsubstituted or substituted by 1 or 2 substituents selected from F, Cl, Br, CF$_3$, NO$_2$, CN, OH, methyl, ethyl, methoxy, dimethylamino, sulfamoyl, methyl-sulfonyl, and methylsulfonylamino;

x is 0, 1, 2, or 3;

y is 1, 2, or 3;

R(7) is hydrogen or alkyl having 1, 2, 3, or 4 carbon atoms;

R(9) is hydrogen or OR(28);

R(28) is hydrogen or alkyl having 1, 2, 3, or 4 carbon atoms;

R(10) and R(11), independently of one another, are hydrogen or alkyl having 1, 2, 3, or 4 carbon atoms;

R(12), R(13), R(14), and R(15), independently of one another, are hydrogen, F, Cl, Br, I, alkyl having 1, 2, 3, 4, or 5 carbon atoms, cycloalkyl having 3, 4, 5, 6, 7, or 8 carbon atoms, CN, CF$_3$, —NO$_2$, or —Y—C$_s$H$_{2s}$—R(29);

Y is —O—, —Co—, —CO—O—, —O—CO—, —S—, —SO—, —SO$_2$—, —O—SO$_2$—, —SO$_2$NR(30)—, —CONR(30)—, or —NR(30)CO—, where the link to the backbone is in each case via the atom on the left;

R(30) is hydrogen or alkyl having 1, 2, or 3 carbon atoms;

s is 0, 1, 2, 3, 4, or 5;

R(29) is hydrogen, methyl, CF$_3$, —OR(31), —COOR(31), —NR(32)R(33), —CONR(32)R(33), or phenyl, where phenyl is unsubstituted or substituted by 1 or 2 substituents selected from F, Cl, Br, CF$_3$, NO$_2$, CN, OH, methyl, ethyl, methoxy, dimethylamino, sulfamoyl, methylsulfonyl, and methylsulfonylamino;

R(31) is hydrogen or alkyl having 1, 2, or 3 carbon atoms;

R(32) and R(33), independently of one another, are hydrogen or alkyl having 1, 2, 3, or 4 carbon atoms; or R(32) and R(33) together form a chain of 4 or 5 methylene groups, of which one CH$_2$ group is optionally replaced by —O—, —S—, —NH—, —N(CH$_3$)—, or —N(benzyl)—.

6. A process for preparing compounds of claim 1, comprising reacting a carboxylic acid of formula IV

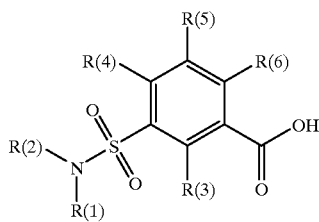

IV in which R(1), R(2), R(3), R(4), R(5), and R(6) have the meanings stated in claim 1, with an amine of formula Va or Vb

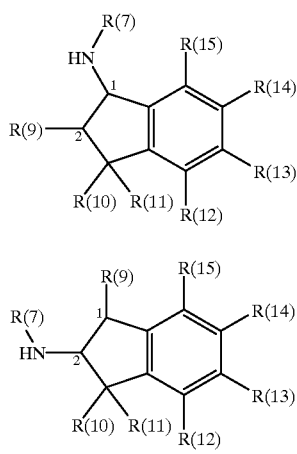

in which R(7), R(9), R(10), R(11), R(12), R(13), R(14), and R(15) have the meanings stated in claim 1, in an amidation reaction.

7. A composition, comprising at least one compound of claim 1 and at least one carrier or additive.

8. A pharmaceutical composition, comprising at least one compound of claim 1 and at least one pharmaceutically acceptable carrier or additive.

9. A pharmaceutical composition of claim 8, further comprising at least one other pharmacological active substance.

10. A composition of claim 9, wherein the other active substance is at least one beta-blocker.

11. A composition of claim 9, wherein the other active substance is at least one $IK_s$-channel blocker.

12. A method for treating and preventing $K^+$-channel mediated diseases, comprising administering to a patient in need thereof an effective amount of at least one compound of claim 1.

13. A method for treating and preventing cardiac arrhythmias which can be eliminated by lengthening the action potential, comprising administering to a patient in need thereof an effective amount of at least one compound of claim 1.

14. A method for treating and preventing re-entry arrhythmias, comprising administering to a patient in need thereof an effective amount of at least one compound of claim 1.

15. A method for treating and preventing supraventricular arrhythmias, comprising administering to a patient in need thereof an effective amount of at least one compound of claim 1.

16. A method for treating and preventing atrial fibrillation or atrial flutter, comprising administering to a patient in need thereof an effective amount of at least one compound of claim 1.

* * * * *

UNITED STATES PATENT AND TRADEMARK OFFICE
CERTIFICATE OF CORRECTION

PATENT NO.   : 6,221,866 B1
DATED        : April 24, 2001
INVENTOR(S)  : Brendel et al.

It is certified that error appears in the above-identified patent and that said Letters Patent is hereby corrected as shown below:

Column 61, claim 1,
Line 5, ".5," should read -- 5, --.
Line 65, "dimethylamine" should read -- dimethylamino --.

Column 62, claim 3,
Line 37, "-C≡-C-, -Co-," should read -- -C≡C-, -CO-, --.
Line 42, "$C_2F_6$" should read -- $C_2F_5$ --.
Line 60, "-N(methyl).-" should read -- -N(methyl)- --.

Column 63, claim 3,
Line 6, "$NH_2$,OH," should read -- $NH_2$, OH, --.
Line 9, "x is0," should read -- x is 0, --.
Line 50, between "or" and "carbon", insert -- 9 --.

Column 65, claim 4,
Line 28, "methylsulfonyl-." should read -- methylsulfonyl- --.

Column 66, claim 5,
Line 21, "-Co-" should read -- -CO- --.

Signed and Sealed this

Eighteenth Day of December, 2001

Attest:

*Attesting Officer*

JAMES E. ROGAN
*Director of the United States Patent and Trademark Office*